(12) United States Patent
Yontz

(10) Patent No.: US 9,301,910 B2
(45) Date of Patent: Apr. 5, 2016

(54) FRAGRANT FORMULATIONS, METHODS OF MANUFACTURE THEREOF AND ARTICLES COMPRISING THE SAME

(75) Inventor: Dorie J. Yontz, Bloomington, MN (US)

(73) Assignee: GFBiochemicals Limited (MT)

( * ) Notice: Subject to any disclaimer, the term of this patent is extended or adjusted under 35 U.S.C. 154(b) by 0 days.

(21) Appl. No.: 13/104,706

(22) Filed: May 10, 2011

(65) Prior Publication Data

US 2011/0274643 A1 Nov. 10, 2011

Related U.S. Application Data

(60) Provisional application No. 61/332,982, filed on May 10, 2010, provisional application No. 61/332,978, filed on May 10, 2010.

(51) Int. Cl.

| | |
|---|---|
| A61K 8/49 | (2006.01) |
| A61Q 13/00 | (2006.01) |
| A61K 8/25 | (2006.01) |
| A61K 8/29 | (2006.01) |
| A61K 8/31 | (2006.01) |
| A61K 8/92 | (2006.01) |
| A61Q 1/04 | (2006.01) |
| A61Q 1/10 | (2006.01) |
| A61Q 1/12 | (2006.01) |
| A61Q 3/00 | (2006.01) |
| A61Q 1/02 | (2006.01) |
| A61Q 1/06 | (2006.01) |
| C09D 7/12 | (2006.01) |
| A01N 25/00 | (2006.01) |
| A61K 8/34 | (2006.01) |
| A61K 8/35 | (2006.01) |
| A61K 8/368 | (2006.01) |
| A61K 8/97 | (2006.01) |
| A61K 47/22 | (2006.01) |
| A61Q 5/10 | (2006.01) |
| A61Q 9/04 | (2006.01) |
| A61Q 15/00 | (2006.01) |
| A61Q 17/04 | (2006.01) |
| C08K 5/156 | (2006.01) |

(52) U.S. Cl.
CPC ............... *A61K 8/498* (2013.01); *A01N 25/00* (2013.01); *A61K 8/25* (2013.01); *A61K 8/29* (2013.01); *A61K 8/31* (2013.01); *A61K 8/34* (2013.01); *A61K 8/35* (2013.01); *A61K 8/368* (2013.01); *A61K 8/4953* (2013.01); *A61K 8/4973* (2013.01); *A61K 8/922* (2013.01); *A61K 8/925* (2013.01); *A61K 8/927* (2013.01); *A61K 8/97* (2013.01); *A61K 47/22* (2013.01); *A61Q 1/02* (2013.01); *A61Q 1/04* (2013.01); *A61Q 1/06* (2013.01); *A61Q 1/10* (2013.01); *A61Q 1/12* (2013.01); *A61Q 3/00* (2013.01); *A61Q 5/10* (2013.01); *A61Q 9/04* (2013.01); *A61Q 15/00* (2013.01); *A61Q 17/04* (2013.01); *C09D 7/1233* (2013.01); *A61K 2800/49* (2013.01); *C08K 5/156* (2013.01)

(58) Field of Classification Search
None
See application file for complete search history.

(56) References Cited

U.S. PATENT DOCUMENTS

| | | |
|---|---|---|
| 1,934,309 A | 11/1933 | Hoover |
| 2,008,720 A | 7/1935 | Lawson |
| 2,260,261 A | 10/1941 | Morey et al. |
| 2,556,135 A | 6/1951 | Croxall et al. |
| 2,654,723 A | 10/1953 | Greene |
| 2,985,536 A | 5/1961 | Stein et al. |
| 3,201,420 A | 8/1965 | Fuzesi et al. |
| 3,658,789 A | 4/1972 | Fried |
| 3,855,248 A | 12/1974 | Lannert et al. |
| 4,460,767 A | 7/1984 | Matsumura et al. |
| 4,737,426 A | 4/1988 | Roth |
| 4,792,411 A | 12/1988 | Walsh |
| 4,806,448 A | 2/1989 | Roth |
| 5,705,087 A | 1/1998 | Mushrush et al. |
| 5,998,092 A | 12/1999 | McCulloch et al. |
| 6,034,118 A | 3/2000 | Bischofberger et al. |
| 6,036,925 A * | 3/2000 | Adams et al. ............... 422/126 |
| 6,306,249 B1 | 10/2001 | Galante et al. |
| 6,372,791 B1 | 4/2002 | Shapiro et al. |
| 6,403,109 B1 | 6/2002 | Stora |
| 6,528,025 B1 | 3/2003 | Boesch et al. |
| 6,806,392 B2 | 10/2004 | Boesch et al. |
| 6,844,302 B1 | 1/2005 | Boden et al. |
| 7,179,775 B2 | 2/2007 | Foster |
| 2002/0183234 A1 | 12/2002 | Jalalian et al. |
| 2003/0007986 A1 | 1/2003 | Stora et al. |
| 2003/0036489 A1 | 2/2003 | Liu et al. |
| 2003/0133895 A1 | 7/2003 | China et al. |
| 2004/0018954 A1 | 1/2004 | Su et al. |

(Continued)

FOREIGN PATENT DOCUMENTS

| | | |
|---|---|---|
| CA | 1000285 | 11/1976 |
| DE | 3220035 A1 | 1/1983 |

(Continued)

OTHER PUBLICATIONS

Oxford English Dictionary definitions of flavor, perfume and fragrance (2014).*
Boehm, R., "Knowledge on cyclic ketals. Part 11: Synthesis of some new derivatives and separation of their isomers," Pharmazie 36(5): 329-330 (1981).
Brigl, et al., "The Reaction of the Pyruvic Acid with Glycerin," Annalen der Chemie 476: 215-232 (Received Oct. 7, 1929)(in German Only).

(Continued)

*Primary Examiner* — Tigabu Kassa
(74) *Attorney, Agent, or Firm* — Cantor Colburn LLP

(57) ABSTRACT

Disclosed herein is a fragrant formulation comprising a fragrant composition, and an alkyl ketal ester. Disclosed herein too are methods for manufacturing the fragrant formulation.

31 Claims, No Drawings

(56) References Cited

U.S. PATENT DOCUMENTS

| | | | |
|---|---|---|---|
| 2004/0024260 A1 | 2/2004 | Winkler et al. | |
| 2004/0120918 A1 | 6/2004 | Lintner et al. | |
| 2004/0138090 A1 | 7/2004 | Drapier et al. | |
| 2004/0167245 A1 | 8/2004 | Chappelow et al. | |
| 2005/0106112 A1* | 5/2005 | Boyd et al. | 424/49 |
| 2005/0245407 A1* | 11/2005 | Ishihara et al. | 510/101 |
| 2006/0069230 A1 | 3/2006 | Papisov | |
| 2006/0134045 A1 | 6/2006 | Cao et al. | |
| 2006/0207037 A1 | 9/2006 | Fadel et al. | |
| 2006/0211855 A1 | 9/2006 | Doring et al. | |
| 2007/0111917 A1 | 5/2007 | Lang et al. | |
| 2008/0081779 A1 | 4/2008 | Holscher | |
| 2008/0124426 A1 | 5/2008 | Kobler et al. | |
| 2008/0242721 A1* | 10/2008 | Selifonov | 514/467 |
| 2008/0305978 A1 | 12/2008 | Wietfeldt et al. | |
| 2010/0087357 A1 | 4/2010 | Morgan, III et al. | |
| 2011/0130470 A1 | 6/2011 | Kraft | |
| 2011/0196081 A1 | 8/2011 | Kwon et al. | |
| 2011/0300083 A1 | 12/2011 | Yontz et al. | |
| 2012/0128614 A1* | 5/2012 | Rieth et al. | 424/70.1 |

FOREIGN PATENT DOCUMENTS

| | | | |
|---|---|---|---|
| DE | 10036423 A1 | | 3/2001 |
| EP | 012543 A1 | | 6/1980 |
| EP | 0308956 A2 | | 3/1989 |
| EP | 0507190 A1 | | 10/1992 |
| EP | 0913463 A1 | | 5/1999 |
| FR | 1445013 | | 7/1966 |
| JP | 284327 | | 9/1953 |
| JP | 2800437 A | | 9/1953 |
| JP | 4217972 | | 8/1992 |
| JP | 07228887 | * | 8/1995 |
| JP | H07228887 A | | 8/1995 |
| JP | 2005143466 | * | 11/2005 |
| JP | 2006022119 A | | 1/2006 |
| JP | 2006143702 A | | 6/2006 |
| JP | 2009035733 A | | 2/2009 |
| JP | 2009179624 A | | 8/2009 |
| SU | 722912 | | 3/1980 |
| WO | 9412489 A1 | | 6/1994 |
| WO | 0193813 A2 | | 12/2001 |
| WO | 2004099173 A1 | | 11/2004 |
| WO | 2005058265 A1 | | 6/2005 |
| WO | 2005095378 A2 | | 10/2005 |
| WO | 2005097723 A2 | | 10/2005 |
| WO | 2005097724 A1 | | 10/2005 |
| WO | 2007062158 A2 | | 5/2007 |
| WO | 2007145994 A2 | | 12/2007 |
| WO | WO2008/046795 A1 | | 4/2008 |
| WO | 2008089463 A2 | | 7/2008 |
| WO | 2008098375 A1 | | 8/2008 |
| WO | 2009065244 A1 | | 5/2009 |
| WO | WO2009/065244 A1 | | 5/2009 |

OTHER PUBLICATIONS

Briol, et al., "Reaction of pyroracemic acid with glycerol," Ann. 476: 215-232 (1929).
Calinaud, et al., "Cyclic acetal series. XIII. Opening of 4-oxo and 4-hydroxy-3,6,8-trioxabicyclo[3.2.1]octane and 3-pxp-2,5,7-trioxabicyclo[2.2.2]octane rings by lithium aluminum hydride and methylmagnesium iodide," Carbohydrate Research 30(1) 35-43 (1973).
Carey, et al., "Advanced Organic Chemistry, Second Edition, Part B: Reactions and Synthesis," Plenum Press 539-552 (1983).
Cuiling, et al., "Synthesis of Levulinic Ketals with Furfuryl Alcohol as Raw Material," Journal of Huagiao University (Nature Science) 23(3): 257-259 (2002) (English Translation).
Eastman Chemical Company. (May 2006). Selecting Coupling Agents for Multi-phase Models. Retrieved Aug. 13, 2009, from http://www.eastman.com/Literature Center/M/M207.pdf.
Gelas, et al., "Synthese du 4-oxo et de 4-hydroxy-3,6,8-trioxabicyclo[3.2.1]octanes," Carbohydrate Research 30(1): 21-34 (1973) (with English abstract).
Grosu, et al., "Stereochemistry and NMR Spectra of Some New Unsymmetrical Substituted 2,2-Dialkyl-1,3-Dioxanes," Revue Roumaine de Chimie 41(3-4): 259-263 (1996).
Gutsche, et al., "Reactions of Ethyl Diazoacetate with Aromatic Compounds Containing Hetero Atoms Attached to the Benzyl Carbon," J. Am. Chem. Soc. 76: 2236-2240 (1954).
Haskelbhrg, L., "The preparation of glycerol esters of amino acids," Compt. rend. 190270-190272 (1930).
Hegde, et al., "The Kinetics and Thermodynamics of Bicyclic Ketal Formation: An Application to the Synthesis of the Zaragozic Acids," Tetrahedron 53(32): 11179-11190 (1997).
Horsfall, et al., "Fungitoxicity of Dioxanes, Dioxolanes, and Methylenedioxybenzenes," The Connecticut Agricultrual Experiment Station New Haven, Bulletin 673: 1-44, Jun. 1965.
Lindblad, et al., "Polymers from Renewable Resources," Advances in Polymer Science 157: 139-161 (2002).
Meltzer, et al., "2,2-Disubstituted 1,3-Dioxolanes and 2,2-Disubstituted 1,3-Dioxanes," JOC 25: 712-715 (1960).
Meskens, Frans A.J., "Methods for the Preparation of Acetals from Alcohols or Oxiranes and Carbonyl Compounds," Synthesis 501-522 (1981).
Nagata, et al., "Synthesis and Applications of [2-Methyl-2(oxoalkyl)-1,3-dioxolan-4-yl] methyl Acrylates for Photocrosslinking Agent," Osaka Kogyo Gijutsu Shikensho Kiho 37(1): 8-16 (1986).
Nakamura, et al., "Study on Ketalization Reaction of Poly (vinyl alcohol) by Ketones. IX. Kinetic Study on Acetalization and Ketalization Reaction of 1,3-Butanediol as a Model Compound for Poly (vinyl alcohol)," Polymer Science Part B: Polymer Physics 35(9): 1719-1731 (2000).
Newman, et al.,"Kinetic and Equilibrium Studies of Cyclic Ketal Formation and Hydrolysis," The Journal of the American Oil Chemist's Society 80: 6350-6355 (1958).
Olson, Edwin S., "Subtask 4.1—Conversion of Lignocellulosic Material to Chemicals and Fuels," Final Report for U.S. Dept. of Energy, National Energy Technology Laboratory, Cooperative Agreement No. DE-FC26-98FT40320 (Jun. 2001).
Ono, et al., "Synthesis and Properties of Soap Types of Cleavable Surfactants Bearing a 1,3-Dioxolane Ring Derived from Long-chain Epoxides and Ethyl Levulinate," J. Jpn. Oil Chem. Soc. 42(12): 965-971 (1993).
Wedmid, et al., "Long-Chain Stereomeric 2-Alkyl-4-methoxycarbonyl-1,3-dioxolanes in Glycerol Acetal Synthesis," J. Org. Chem. 42(22): 3624-3626 (1977).
Yamaguchi, Masahiko, "Synthesis of Polycyclic Aromatic Compounds via Polyketides," Yuki Gosei Kagaku Kyokaishi 45(10) 969-982 (1987) (Chinese—Translation of Abstract Only).
Yang, et al., "Investigation of homopolymerization rate of perfluoro-4,5-substituted-2-methylene-1,3-dioxolane derivatives and properties of the polymers," Journal of Flourine Science 127: 277-281 (2006).
Zhang, et al., "Synthesis of Ketals of 4-Oxopentanoates," Lanzhou Daxue Xuebao, Ziran Kexueban 30(2): 66-70 (1994).
International Search Report for PCT/US2011/035956, mailed Feb. 8, 2012, 4 pages.
Transmittal and International Search Report for PCT/2011/035973, mailed Feb. 8, 2012, 6 pages.
Written Opinion of the International Searching Authority for PCT/US2011/035956, mailed Feb. 8, 2011, 6 pages.
Written Opinion of the International Searching Authority for PCT/2011/035973, mailed Feb. 8, 2011, 7 pages.
International Preliminary Report on Patentability for International Application No. PCT/US2011/035956, mailed Nov. 13, 2012, 8 pages.
Transmittal and International Search Report for PCT/US2011/050651, maield Apr. 26, 2012, 6 pages.
Written Opinion of the International Searching Authority for PCT/US2011/050651, mailed Apr. 26, 2012, 7 pages.
Brigl, Percy, et al., "The Reaction of the Pyruvic Acid with Glycerin," Annalen der Chemie 476: p. 215-232, Received Oct. 7, 1929, (with English translation).

(56) References Cited

OTHER PUBLICATIONS

Hexyl CELLOSOLVE(R) Solvent, DOW Technical Data Sheet, 3 pages (2012).
Holmberg, Krister, "Surfactants with controlled half-lives", Current Opinion in Colloid & Interface Science, vol. 1, Issue 5, pp. 572-579 (Oct. 1996).
Tang, Jian, "Synthesis and Application of Fructone", Contemporary Chemical Industry, vol. 38, No. 3, Jun. 30, 2009, pp. 312-314, with English abstract.
Fu, Hongbo, "Synthesis and Application of Fructose", Application of Toothpaste, No. 3, pp. 23-24, with English Abstract.
STIC Search Report dated Jul. 5, 2013, 90 pages.
IPRP, Issued Apr. 2, 2015.
Japan Notice of Reasons for Rejection for Japan Application No. 2013-510256; Rejection Date Mar. 13, 2015; Mailing Date: Mar. 24, 2015, 6 pages, English Translation begins on p. 4.
Black, Cline, et al., "The Solubility of Water in Hydrocarbons", The Journal of Chemical Physics, vol. 16, pp. 537-543 (1948).
Chinese Search Report for 201180023186.7 dated Sep. 27, 2013, 3 pages.
Chinese Search Report from Second Office Action for Appln. No. 201180023186.7, issued Jun. 20, 2014 (English translation), 12 pages.

* cited by examiner

FRAGRANT FORMULATIONS, METHODS OF MANUFACTURE THEREOF AND ARTICLES COMPRISING THE SAME

CROSS-REFERENCE TO RELATED APPLICATIONS

This application claims the benefit of U.S. Provisional Application No. 61/332,978, filed May 10, 2010, which is incorporated herein by reference in its entirety, and to U.S. Provisional Application No. 61/332,982, filed May 10, 2010, which is incorporated herein by reference in its entirety.

FIELD OF THE INVENTION

This disclosure relates to perfume and flavorant formulations (hereinafter jointly referred to as fragrant formulations). More specifically, the present invention is directed to fragrant formulations, which employ alkyl ketal esters as solvents, co-solvents, or fixatives.

BACKGROUND

Flavor is the sensory impression of a food or of another substance and is determined mainly by the chemical senses of taste and smell. The "trigeminal senses," which detect chemical irritants in the mouth and throat as well as temperature and texture, are important to the overall Gestalt of flavor perception. The flavor of a food can be altered with natural or artificial flavorants, which affect these senses. Flavor compounds are sold to the food and beverage industries for use in consumer products such as prepared foods, beverages, dairy, food and confectionery products.

Flavorants are defined as substances that give another substance flavor, altering the characteristics of the solute, causing it to become sweet, sour, tangy, or the like. Of the three chemical senses, smell is the main determinant of a foods flavor. While the taste of food is limited to sweet, sour, bitter, salty, and savory (umami)—the basic tastes—the smells of a food are potentially limitless. A food's flavor, therefore, can be easily altered by changing its smell while keeping its taste similar. Nowhere is this better exemplified than in artificially flavored jellies, soft drinks and candies, which, while made of bases with a similar taste, have dramatically different flavors due to the use of different scents or fragrances. The flavorings of commercially produced food products are generally created by flavorists.

Although the terms "flavoring" or "flavorant" in common language denotes the combined chemical sensations of taste and smell, the same terms are usually used in the fragrance and flavors industry to refer to edible chemicals and extracts that alter the flavor of food and food products through the sense of smell. Due to the high cost or unavailability of natural flavor extracts, most commercial flavorants are nature-identical, which means that they are the chemical equivalent of natural flavors but are chemically synthesized rather than being extracted from the source materials. Flavorants are added to beverages, food items, and to health care products (e.g., toothpaste, mouthwash, and the like) in much the same manner and for some of the same reasons as perfumes are added to solid substrates or to gases, namely to enhance odor or to camouflage malodors.

Fragrant formulations are added to a variety of products to deliver an odor. For example, these fragrant formulations are often added to consumer products to deliver a fresh (or clean) odor to targeted substrates (such as textiles, hard surfaces, skin, hair, and the like) and to provide an olfactory aesthetic benefit. They are often added to gases and to industrial products to camouflage malodors (e.g., air fresheners, candles) or added to odorless gases to facilitate detection (e.g., methane and carbon monoxide).

Substantive fragrant compositions (also known as "enduring fragrances") are those that effectively deposit onto a substrate in, for example, a cleaning process or a food product and are detectable by the olfactory system. Persons skilled in the art of creating fragrant formulations usually have some knowledge of particular fragrant compositions that are substantive (in general, such ingredients are heavy, insoluble and non-volatile).

Fragrant compositions are often combined with other ingredients, such as solvents, to create fragrance formulations. Solvents can be used for solubilizing or compatibilizing various components in the fragrance formulation, or other ingredients useful for making a final product that meets the desired performance criteria.

SUMMARY

It is desirable to replace current solvents in fragrance formulations with other solvents that do not have disadvantages. In other cases, there is a need to reduce the quantities of the various formulary components in order to reduce costs and simplify formulating. There is also a need to increase the solubility of the ingredients in order to produce a concentrate or to dissolve a relatively insoluble ingredient. There may also be a need to dissolve a wide variety of ingredients in a single composition. It is to solving these needs the present invention is directed.

In one aspect, the invention is a fragrant formulation comprising at least one fragrant composition, and an alkyl ketal ester of formula (I)

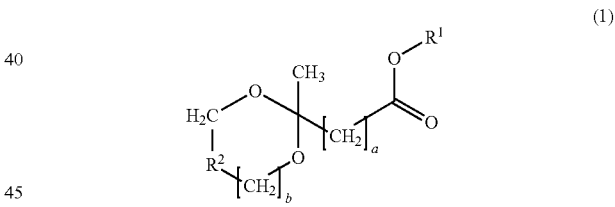

wherein a is 0 or an integer of 1 to 12; b is 0 or 1; $R^2$ is a divalent $C_{1-8}$ g group optionally substituted with up to 5 hydroxyl groups; and $R^1$ is $C_{1-6}$ alkyl.

In another aspect, the invention is a method comprising blending a fragrant composition and an alkyl ketal ester of formula (I)

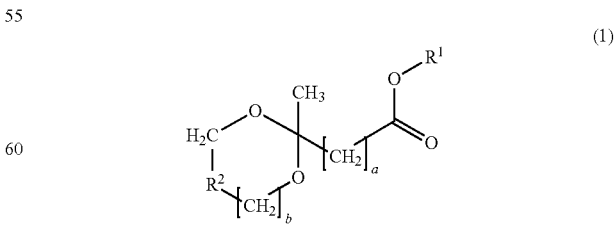

wherein a is 0 or an integer of 1 to 12; b is 0 or 1; $R^2$ is a divalent $C_{1-8}$ group optionally substituted with up to 5 hydroxyl groups; and $R^1$ is $C_{1-6}$ alkyl.

In yet another aspect, the invention is an article comprising a fragrant composition and an alkyl ketal ester of formula (I):

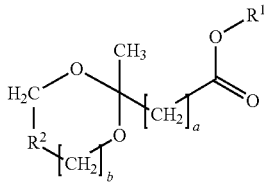

wherein a is 0 or an integer of 1 to 12; b is 0 or 1; $R^2$ is a divalent $C_{1-8}$ group optionally substituted with up to 5 hydroxyl groups; and $R^1$ is $C_{1-6}$ alkyl.

DETAILED DESCRIPTION

As used herein, the term "fragrant composition" refers to a fragrant compound, such as the active aroma compound (either odor or flavor or both). The fragrant composition can be a single aroma ingredient or a mixture of aroma ingredients.

As used herein, the term "perfume composition" refers to fragrant compositions that are for odor purposes.

As used herein, the term "flavorants" or "flavorant composition" refers to fragrant compositions that are used for taste purposes.

As used herein, the term "fragrance formulation" refers to the fragrant composition plus a solvent plus optionally other additional components. A fragrance formulation can be for flavor or odor or both.

As used herein, the term "perfume formulation" is a formulation form specifically for odor purposes. It can contain a perfume composition (i.e., the odor molecules) in addition to solvents and optionally other additional components.

Efforts continue to be made to find improvements in the performance of fragrant formulations, including their in-product shelf life, their delivery effectiveness, and their longevity or substantivity on various substrates. For example, during use, a substantial amount of perfume in a cleaning product is lost with rinse water and through drying. It is desirable to be able to overcome these process conditions and to ensure that the perfume material left on the substrate provides a maximum odor effect via the minimum amount of material, i.e., there is a need to be able to create highly substantive perfume materials.

As discussed above, fragrant compositions are often combined with other ingredients, such as solvents, to create fragrance formulations. Solvents can be used for solubilizing or compatibilizing various components in the fragrant formulation, or other ingredients useful for making a final product that meets the desired performance criteria. Ethanol constitutes a good solubilizing agent for fragrance ingredients, and additionally has the advantage of being inexpensive and of allowing the formulation of transparent formulations. It however, has the disadvantage of adversely affecting the olfactory characteristics of the fragrant composition, not only because of its potent odor but also because of its capacity to react with the fragrant composition and to thereby modify the odor and/or the color. It is also capable of chemically reacting with atmospheric nitrogen oxides to form ozone, which constitutes, in this regard, a source of atmospheric pollution. Moreover, ethanol is subject to VOC (volatile organic compound) regulations in certain jurisdictions. Efforts are therefore being made to avoid ethanol. Ethanol is also an irritant and may be a source of tingling when it is applied to sensitive or damaged skin, in particular after shaving.

Disclosed herein are fragrant formulations that comprise a fragrant composition and an alkyl ketal ester. The fragrant formulation offers a broad combination of properties that allows it to be advantageously used in a variety of applications such as antiperspirants, deodorants, cleansers, soaps, perfumes, colognes, candles, furniture polishes, chemicals and the like. In one embodiment, the fragrant formulation can be used in drinks, foods, snacks, healthcare products, and other edible items.

The broad solubilities and solubilization capabilities of the alkyl ketal esters render them useful in a broad variety of fragrant formulations including aqueous and organic formulations. The alkyl ketal esters are particularly useful in mixed aqueous-organic fragrant formulations and in fragrant formulations that are non-aqueous that contain waxes. A further advantage is that certain types of the alkyl ketal esters, such as the levulinate ester ketals, can be derived from biological feedstocks. The alkyl ketal esters can advantageously be used both as solvents as well as fixatives in the fragrant composition.

In one embodiment, the alkyl ketal esters may be used to extract essential oils and fragrant molecules from naturally occurring substances. The solubilizing capabilities of the alkyl ketal esters may be advantageously used to extract the essential oils. Following the extraction, the extract may be further treated with other additives and used as a fragrant formulation in consumer goods, industrial products, foods and beverages. If the alkyl ketal esters are used in the extraction of an essential oil, then there may not be a need to add additional alkyl ketal esters to the final fragrant formulation. Alternatively, it may be desirable to remove some of the alkyl ketal esters used in the extraction from the essential oil in order to provide the fragrant formulation with desired properties.

Fragrant formulations are generally created to have top, middle, and base notes for a particular sensory profile that evolves during the user's exposure (such as evolving odor as the product evaporates or evolving flavor as the product is consumed). The top, middle and base notes may have separate sensory characteristics and supporting ingredients. In one embodiment, the alkyl ketal esters can effectively function as a fragrance fixative, prolonging the effect of the fragrant formulation and so prolonging fragrance life.

The alkyl ketal esters useful herein include those having the general structure I

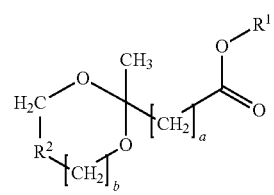

wherein a is 0 or an integer of 1 to 12, specifically 1 to 6, more specifically 1 to 4; b is 0 or 1;
$R^2$ is a divalent $C_{1-8}$ group optionally substituted with up to 5 hydroxyl groups, specifically methylene, ethylidene (>CH—$CH_3$), >CH—$CH_2OH$, >C($CH_3$)$CH_2OH$, >C($C_2H_5$)$CH_2OH$, >C($CH_2OH$)$_2$, >CH—CH(OH)—$CH_2OH$, or >CH—(CHOH)$_3$—$CH_2OH$; and $R^1$ is $C_{1-6}$ alkyl, specifically $C_{1-4}$ alkyl. Some compounds within the scope of Structure I contain one or more chiral carbon atoms, as is the case where b is 0 or $R^2$ is substituted; structure I does not distinguish among those possible stereoisomers and is intended to include all such stereoisomers. In a specific embodiment, a is 1 to 4, b is 0 or 1, and $R^2$ is >CH—CH$_3$, >CH—CH$_2$OH, >C(CH$_3$)CH$_2$OH, >C(C$_2$H$_5$)CH$_2$OH, >C(CH$_2$OH)$_2$, >CH—CH(OH)—CH$_2$OH, or >CH—(CHOH)$_3$—CH$_2$OH.

When b is 0, the alkyl ketal ester includes a five-membered ring; when b is 1, it includes a six-member ring. In a specific embodiment b is 0.

In some embodiments, b is 0 and $R^2$ is one of methylene, ethylidene or >CH—CH$_2$OH. In other embodiments, b is 1 and $R^2$ is methylene.

In an embodiment, $R^1$ contains 1 or 2 carbon atoms.

Specific alkyl ketal esters include those corresponding to the reaction formulations of 1,2-ethylene glycol with the methyl, ethyl, n-propyl or n-butyl ester of levulinic acid; of 1,2-propylene glycol with the methyl, ethyl, n-propyl or n-butyl ester of levulinic acid; of 1,3-propane diol with the methyl, ethyl, n-propyl or n-butyl ester of levulinic acid; of glycerine with the methyl, ethyl, n-propyl, or n-butyl ester of levulinic acid; of trimethylolethane with the methyl, ethyl, n-propyl, or n-butyl ester of levulinic acid; of trimethylolpropane with the methyl, ethyl, n-propyl, or n-butyl ester of levulinic acid; of pentaerythritol with the methyl, ethyl, n-propyl, or n-butyl ester of levulinic acid; of erythritol with the methyl, ethyl, n-propyl, or n-butyl ester of levulinic acid; of sorbitol with the methyl, ethyl, n-propyl, or n-butyl ester of levulinic acid; of 1,2-ethylene glycol with methyl, ethyl, n-propyl, or n-butyl acetoacetate; of 1,2-propylene glycol with methyl, ethyl, n-propyl, or n-butyl acetoacetate; of 1,3-propane diol with methyl, ethyl, n-propyl, or n-butyl acetoacetate, of glycerine with methyl, ethyl, n-propyl, or n-butyl acetoacetate; of trimethylolethane with methyl, ethyl, n-propyl or n-butyl acetoacetate; of trimethylolpropane with methyl, ethyl, n-propyl, or n-butyl acetoacetate, or erythritol with methyl, ethyl, n-propyl, or n-butyl acetoacetate; of pentaerythritol with methyl, ethyl, n-propyl, or n-butyl acetoacetate; or of sorbitol with methyl, ethyl, n-propyl, or n-butyl acetoacetate.

Specific alkyl ketal esters include those having the following structures II-VI. An embodiment includes alkyl ketal esters of structure II

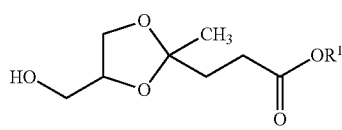

(II)

wherein $R^1$ is methyl, ethyl, n-propyl, or n-butyl. When $R^1$ is methyl, this structure is referred to herein as "methyl-LGK," and corresponds to the reaction formulation of methyl levulinate with glycerine. Methyl-LGK is miscible with water in all proportions.

When $R^1$ in structure II is ethyl, this structure is referred to herein as "ethyl-LGK," or "Et-LGK" and corresponds to the reaction formulation of ethyl levulinate with glycerine. Ethyl-LGK is miscible in water in all proportions. Ethyl-LGK also dissolves or is miscible with a large number of hydrophobic and hydrophilic organic compounds to the extent of at least 20 parts of the organic compound in 80 parts of ethyl-LGK. Examples of such organic compounds include methanol, ethanol, tetrahydrofuran, acetone, ethyl acetate, ethyl laurate, lauric acid, methylene chloride, toluene, acetic acid, low molecular weight poly(propylene glycol), and castor oil.

When $R^1$ in structure II is n-propyl, this structure is referred to herein as "n-propyl-LGK," and corresponds to the reaction formulation of n-propyl levulinate with glycerine. n-Propyl-LGK is miscible with water to the extent of 1 part per 99 parts water.

When $R^1$ in structure II is n-butyl, this structure is referred to herein as "n-butyl-LGK" or "Bu-LGK," and represents the reaction formulation of n-butyl levulinate with glycerine. n-Butyl-LGK is miscible in water to the extent of 1 part per 99 parts of water. It dissolves or is miscible with various organic compounds to the extent of at least 20 parts of the organic compound in 80 parts of N-butyl-LGK. Examples of such organic compounds include alcohols (including ethanol and 1,2-butylene glycol), organic esters (such as $C_{12-14}$ alkyl benzoates, isopropyl myristate and octyl palmitate), and many vegetable oils (including castor, corn, soy and safflower oils).

Another embodiment includes alkyl ketal esters of structure III

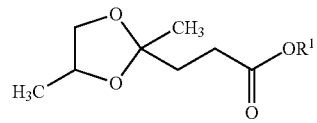

(III)

wherein $R^1$ is methyl, ethyl, n-propyl, or n-butyl. When $R^1$ is methyl, the structure is referred to herein as "methyl-LPK" and corresponds to the reaction formulation of methyl levulinate with 1,2-propylene glycol.

When $R^1$ in structure III is ethyl, this structure is referred to herein as "ethyl-LPK" or "Et-LPK," and corresponds to the reaction formulation of ethyl levulinate with 1,2-propylene glycol. Ethyl-LPK is miscible in water to the extent of 2.5 parts in 97.5 parts of water. Ethyl-LPK dissolves or is miscible with a variety of organic compounds of varying hydrophilicity, to the extent of at least 20 parts of the organic compound in 80 parts of ethyl-LPK. These organic compounds include, for example, methanol, ethanol, tetrahydrofuran, acetone, ethyl acetate, methylene chloride, toluene, cyclohexane, acetic acid, low molecular weight poly(propylene glycol), mineral oil, castor oil, canola oil, corn oil, and sunflower oil.

When $R^1$ in structure III is n-butyl, this structure is referred to herein as "n-butyl-LPK" or "Bu-LPK," and represents the reaction formulation of n-butyl levulinate with 1,2-ethylene glycol. n-butyl-LPK dissolves or is miscible with various organic compounds to the extent of at least 20 parts of the organic compound in 80 parts of N-butyl-LPK. Examples of such organic compounds include alcohols (including ethanol and 1,2-butylene glycol), organic esters (such as $C_{12-14}$ alkyl benzoates, isopropyl myristate and octyl palmitate), and many vegetable oils (including castor, corn, soy and safflower oils).

Another embodiment includes alkyl ketal esters of structure IV

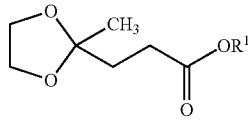

(IV)

wherein R¹ is methyl, ethyl, n-propyl, or n-butyl. When R¹ is ethyl, this structure is referred to herein as "ethyl-LEK," and corresponds to the reaction formulation of ethyl levulinate with 1,2-ethylene glycol. Ethyl-LEK is miscible in water to the extent of 5 parts per 95 parts of water.

Another embodiment includes alkyl ketal esters of structure V

(V)

wherein R¹ is methyl, ethyl, n-propyl, or n-butyl. When R¹ is methyl, this structure is referred to herein as "Me-AcAcGK," and represents the reaction formulation of methyl acetoacetate with glycerine. When R¹ is ethyl, this structure is referred to herein as "Et-AcAcGK," and represents the reaction formulation of ethyl acetoacetate with glycerine. Me-AcAcGK and Et-AcAcGK each are miscible with water in all proportions.

Another embodiment includes alkyl ketal esters of structure VI

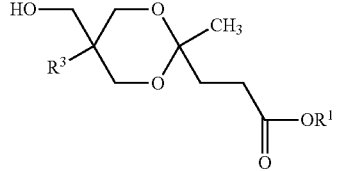
(VI)

wherein R¹ is methyl, ethyl, n-propyl or n-butyl and R³ is methyl or ethyl. Compounds according to structure VI correspond to the reaction formulation of trimethylolethane (R³ is methyl) or trimethylolpropane (R³ is ethyl) and a $C_{1-4}$ ester of levulinic acid. When R¹ is ethyl, and R³ is methyl, this structure is referred to herein as "ethyl-MeLTMEK," and when R¹ is ethyl, and R³ is ethyl, this structure is referred to herein as "ethyl-EtLTMPK."

The alkyl ketal esters of structures I-VI can be prepared by reacting an alkyl keto ester of structure VII

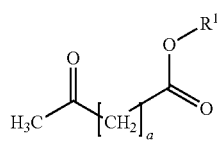
(VII)

with the appropriate polyol of structure VIII

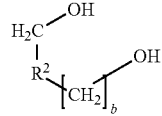
(VIII)

wherein a, b, R² and R¹ are as defined in structure I. Specific ketoesters include $C_{1-4}$ alkyl esters of pyruvic acid, acetoacetic acid, levulinic acid, α-ketobutyric acid, α-ketoisovaleric acid, 5-ketohexanoic acid, α-ketoisocaproic acid, 4-acetylbutyric acid, 2-ketopentanoic acid, 3-ketohexanoic acid, 4-ketohexanoic acid, 2-ketooctanoic acid, 3-ketooctanoic acid, 4-ketooctanoic acid, 7-ketooctanoic acid, 2-keto-4-pentenoic acid, and 2-oxo-3-butynoate. Specific polyols include ethylene glycol, 1,2-propylene glycol, 1,3-propane diol, glycerine, trimethylolethane, trimethylolpropane, erythritol, pentaerythritol, or sorbitol. This reaction can be performed in the presence of an acid catalyst. A preferred process is described in WO 09/032,905.

In preferred embodiments, the keto ester is a $C_1$-$C_4$ alkyl ester of levulinic acid (4-oxopentanoic acid). Levulinic acid is an abundant feedstock that is prepared on an industrial scale by acidic degradation of hexoses and hexose-containing polysaccharides such as cellulose, starch, sucrose, and the like. Other preferred keto esters include $C_1$-$C_4$ alkyl esters of pyruvic acid and acetoacetic acid. Especially preferred keto esters include ethyl levulinate, n-propyl levulinate, and n-butyl levulinate.

The term "miscible" and its variations ("miscibility", "compatibility", and the like) are used herein as a synonym for "soluble", i.e., a mixture of the materials by themselves form a "true" solution, in which one material is molecularly dispersed in the other, or in which one material is dispersed as droplets which have a longest dimension of less than 200 nm, such that the mixture is optically clear. In an exemplary embodiment, the longest dimension is a "radius of gyration". As used herein, a material that is "miscible" or "fully miscible" in another, without further qualification, is miscible with that other material in all proportions, i.e., in mixtures that contain the two components by themselves in all weight ratios from 99:1 to 1:99. For example, a fully water miscible alkyl ketal ester is soluble water at all proportions from 99:1 to 1:99. A partially miscible alkyl ketal ester is immiscible in another material in proportions from greater than 30 parts of the alkyl ketal ester in 70 parts or less of the other material and miscible in other combinations. A sparingly miscible alkyl ketal ester is immiscible in another material in proportions from greater than 10 parts of the alkyl ketal ester in 90 parts or less of the other material and miscible in other combinations. A material is "immiscible" in another if it is not soluble by itself in that material to the extent of at least 1 part per 99 parts of the other. Unless stated otherwise, miscibility is assessed at 25° C. The foregoing alkyl ketal esters can be classified as fully water-miscible, partially water-miscible, or sparingly water-miscible.

By "macroscopically uniform," it is meant that the formulation is uniform when viewed at a length scale of at least 10 micrometers.

The selection of a particular alkyl ketal ester for a particular fragrance formulation will depend at least in part upon the function that the alkyl ketal ester is expected to perform in the formulation, as well as the other ingredients of the formulation. For example, when the alkyl ketal ester is present to solubilize an ingredient, such as an active agent into an aqueous phase, a partially- or fully-water miscible alkyl ketal ester is selected. If the active agent is highly hydrophobic, a mixture of a partially- or fully-water miscible alkyl ketal ester with a sparingly water-miscible alkyl ketal ester can be used.

When the alkyl ketal ester is present to solubilize a fragrant composition into an alcoholic phase or an alcohol/water mixture, the alkyl ketal ester is preferably miscible in the alcohol to the extent of at least 30 parts in 70 parts of the alcohol, and can be fully miscible in the alcohol. Alkyl ketal esters that are fully or partially soluble in the alcohol can be present in a mixture with one or more alkyl ketal esters that are only sparingly soluble in the alcohol. This can allow, for example, the alcohol/miscible alkyl ketal ester mixture to function as a cosolvent mixture in which the sparingly soluble alkyl ketal ester is dissolved. The sparingly soluble alkyl ketal ester can in turn carry yet another material into the solution. The alcohol in such an alcoholic phase or alcohol/water mixture is a lower alcohol including C1-7 alkanols such as ethanol, 1-propanol, 2-propanol, 1-butanol, 2-butanol, t-butanol, 1-pentanol, 1-hexanol, as well as the various other isomers of pentanol and hexanol; alkylene glycols such as ethylene glycol, diethylene glycol, triethylene glycol, 1,2-propylene glycol, 1,3-propane diol, dipropylene glycol, tripropylene glycol 1,4-butane diol and 1,2-butane diol; triols such as glycerine, and the like, and is preferably ethanol, isopropanol, 1,2-propylene glycol, or 1,3-propane diol.

When the alkyl ketal ester is present to dissolve a fragrant composition into an oil phase, the alkyl ketal ester can be a partially-water miscible type or a sparingly water-miscible type. It is also possible in some cases to use fully-water-miscible types in that instance.

When a fragrance formulation comprises an aqueous solution (containing, for example, at least 35% by weight water based on the weight of the fragrant formulation) or comprises an aqueous gel in which the fragrant composition is dissolved, the alkyl ketal ester is preferably a fully water-miscible type such as methyl-LGK, ethyl-LGK, methyl-AcAcGK, or a mixture of one or more of them with a partially water-miscible alkyl ketal ester and/or a sparingly soluble alkyl ketal ester such as propyl-LGK, ethyl-LPK, ethyl-LEK and the like.

Fragrant formulations which take the form of alcohol or alcohol-water solutions (in which the water content is less than 35% of the fragrance formulation, and can be less than 20%, less than 10% or less than 5% of the combined weight of the water plus the alcohol in which a fragrant composition is dissolved) can contain, such as in the case of ethanol, isopropanol, and 1,2-propylene glycol, fully water-miscible alkyl ketal esters, partially water-miscible alkyl ketal esters, sparingly water-miscible alkyl ketal esters, or mixtures thereof. Partially and fully water-miscible alkyl ketal esters can form a single-phase solution with ethanol, isopropanol, 1,2-propylene glycol, into which additional materials can be dissolved, or an organic phase can be dispersed. Gels containing alcohol or alcohol-water solutions in which a gel is suspended can similarly contain fully water-miscible alkyl ketal esters, partially water-miscible alkyl ketal esters, sparingly water-miscible alkyl ketal esters, or mixtures thereof, depending on the alcohol used as described above for alcohol and alcohol-water solutions.

Fragrant formulations in the form of an emulsion of an oil phase and an aqueous phase (including, for example, lotions and creams) and in which the alkyl ketal ester performs a compatibilizing or emulsifying function between the phases can contain a fully water-miscible alkyl ketal ester such as methyl-LGK, ethyl-LGK, methyl-AcAcGK, or partially water-miscible type or a mixture of one or more of them with a sparingly soluble alkyl ketal ester such as propyl-LGK, ethyl-LPK, ethyl-LEK and the like.

Fragrant formulations in which the alkyl ketal ester is present in an oil phase (such as to dissolve or compatibilize components within an oil phase) can contain a partially or fully water-miscible alkyl ketal ester, a sparingly soluble alkyl ketal ester such as propyl-LGK, ethyl-LPK, n-butyl-LPK, ethyl-LEK and the like, or a mixture of one or more of a sparingly water-miscible alkyl ketal ester with a partially- or fully-water miscible alkyl ketal ester.

Waxy fragrant formulations such as candles, polishes, lip balms or other hydrophobic formulations in which the alkyl ketal ester is called upon to compatibilize water or other polar compounds into the formulation typically include a fully water-miscible of alkyl ketal ester such as methyl-LGK, ethyl-LGK, methyl-AcAcGK, or partially water-miscible type, but can also include a sparingly-miscible type.

Many fragrant formulations are combinations of two or more fragrant compositions. For example, some fragrant formulations contain an aqueous phase that contains a dissolved fragrant composition, and further includes an oil phase, which can be present, for example, to supply emollients and/or humectants, or to produce a specific formulation form (cream, lotion and the like). In such cases, it is possible to include two or more alkyl ketal esters within the fragrant formulation to perform different functions. Thus, for example, a fully-water-miscible alkyl ketal ester might be present in the aqueous phase to help dissolve the fragrant composition, and a partially-or sparingly water-miscible alkyl ketal ester might be present within the oil phase to reduce its viscosity or compatibilize its components. Either of these alkyl ketal esters can also perform some emulsifying or compatibilizing function between the aqueous and oil phases or materials within each phase.

In addition, a single alkyl ketal ester or blend of alkyl ketal esters can perform multiple functions within a fragrant formulation, such as dissolving an active agent into an aqueous or oil phase, compatibilizing or emulsifying an aqueous phase with an oil phase, and the like. Examples of active agents that can be utilized in these formulations are known to those of skill in the art and are also disclosed in co-pending U.S. patent application Ser. No. 13/104,570, which is hereby incorporated by reference in its entirety for all purposes. In addition, a single alkyl ketal ester can perform multiple functions within a fragrant formulation, such as dissolving an active agent into an aqueous or oil phase, compatibilizing or emulsifying an aqueous phase with an oil phase, compatibilizing the fragrant composition with other solvents used in the fragrant formulation, and the like.

The alkyl ketal ester can reside in an aqueous phase, in an alcoholic or alcohol-water phase, in a wax phase, or in an oil phase of a fragrant formulation, depending on the particular fragrant formulation and the particular alkyl ketal ester. In many cases, an alkyl ketal ester can become distributed between aqueous and oil phases of a fragrant formulation, due to its solubility in both phases. In some cases, the alkyl ketal ester can reside at the boundary of aqueous and oil phases.

The amount of alkyl ketal ester present in a fragrant formulation depends on the function of the alkyl ketal ester, the other ingredients of the fragrant formulation, the specific form of the fragrant formulation, and like considerations.

In general, the fragrant formulation comprises about 10 to about 80 wt %, specifically about 15 to about 70 wt %, and more specifically about 20 to about 60 wt % of the alkyl ketal ester, based on the total weight of the fragrant formulation.

As noted above, the fragrant formulation may be further diluted with additional ingredients such as, for example, solvents, surfactants, and the like to form a fragrant formulation. The fragrant formulation may comprise the fragrant composition in an amount of about 0.001 to about 10 wt %, specifically about 0.1 to about 5 wt % and more specifically about 1 to about 4 wt %, based on the total weight of the fragrant formulation.

In addition to solubilization, the alkyl ketal ester can be effective coupling solvents. Coupling solvents act to solubilize two components that are wholly or partially immiscible in the absence of the coupling solvent, for example, mixtures of oil and water. Effective coupling solvents generally have both lipophilic and hydrophilic character. There are a variety of reasons why coupling may be desirable in a fragrant formulation. Many fragrant ingredients, for example, aldehydes, esters, and the like, have some polarity and may separate from nonpolar substrates (e.g., candles). Phase separation can lead to aesthetic problems like insoluble droplets or particles settling at the bottom of the product. Another polarity problem arises when the fragrant composition sublimates from solid to gas to solid; if these molecules separate from the formulation base, they can sublimate and then recondense, forming a film on the container. In some product forms, an optically transparent fragrant formulation is desired and a coupling solvent can help to maintain clarity in the product formulation after the fragrant composition is added.

As noted above, the alkyl ketal ester can also serve as useful fixatives because of their higher boiling points compared to many fragrant moieties. A fixative is used to support the primary scent by bolstering it. The fragrant compositions generally have top, middle, and base notes that have separate primary scents or olfactory characteristics. These notes are created carefully with knowledge of the evaporation process of the formulation. Top notes are those scents that are perceived immediately on application of a fragrance. Top notes consist of small, light molecules that evaporate quickly. They form a person's initial impression of a fragrant formulation and thus are very important in the selling of a product. They are also called the head notes. The middle notes represent the scent or olfactory sensation of a fragrance that emerges just prior to when the top notes dissipate. The middle note compounds form the "heart" or main body of a fragrance formulation and act to mask the often unpleasant initial impression of base notes, which become more pleasant with time. Middle notes are also called the heart notes. The base notes represent the scent of a fragrance that appears close to the departure of the middle notes. The base and middle notes together are the main theme of a fragrance formulation. Base notes bring depth to a fragrance. Compounds of this class of fragrances are typically rich and "deep" and are usually not perceived until about 30 minutes after application. The fragrances in the top and middle notes are influenced by the base notes, as well the fragrances of the base notes will be altered by the type of fragrance materials used as middle notes.

In one embodiment, the alkyl ketal ester can be used as a fixative for a particular note in a fragrance formulation. Other fixatives may then be used to fix the other notes in the fragrance formulation. The alkyl ketal ester can also be used in conjunction with the other fixatives to fix a particular note in the fragrance formulation.

In another embodiment, one or more alkyl ketal ester may be used as a fixative for one or more notes in the fragrance formulation. The alkyl ketal ester can be used as fixatives for top notes, middle notes and base notes. For example, an alkyl ketal ester having a molecular weight of about 130 to about 300 grams per mole can be used as a fixative for the top notes, while an alkyl ketal ester having a molecular weight of about 300 to about 450 grams per mole can be used as a fixative for the middle notes, while an alkyl ketal ester having a molecular weight of about 450 to about 1,000 grams per mole may be used as a fixative for the base notes.

A fragrant composition can also be a flavorant and may be used for flavoring foods, beverages or healthcare products to produce various sensations. The sensations may be sweet, sour, spicy, pungent, bitter, or the like and may be used in articles such as hard candy, chewing gum, mayonnaise, sour cream, onion and other vegetable dips, potato chip snacks, alcoholic cordial, mouthwash, toothpaste, and the like. A detailed list of essential oils and fragrant molecules that can act as flavorants and/or fragrances is listed below. It is to be noted that some of the flavorants are fragrances as well. Likewise, a fragrance formulation can include not only fragrant compositions for odor purposes but also fragrant compositions for flavoring.

The alkyl ketal ester can be used to reduce the surface tension of solvents such as water that are frequently used in fragrance formulations. The surface tension of water is quite high among common liquids and arises from the polar nature of the water molecule. For a liquid to wet the surface of a solid, the surface tension of the liquid must be lower than the solid surface tension. So, while water is generally a preferred carrier because of its low cost and low flammability, its surface tension must be reduced in many applications so it can spread and wet surfaces. The alkyl ketal esters in particular demonstrate the ability to effectively reduce surface tension of aqueous solutions without the environmental and volatile organic compound (VOC) issues affiliated with other solvents.

The alkyl ketal esters are further advantageous due to their low volatility. Volatility manifests itself in a number of key properties for solvents, including boiling point, vapor pressure, relative evaporation rate, flammability, odor, and volatile organic compound content. The desired volatility profile of a solvent varies considerably by application, and there are often conflicting considerations. For instance, highly volatile process solvents require less energy to remove after use, but in many cases also require special handling due to higher flammability. Appropriate selection of each of the specific $R^1$, $R^2$, a and b in the Formulas (I) through (VIII) can further provide a selected volatility and solubilizing capacity. The alkyl ketal esters thus have excellent combination of properties for use in these applications, including solubilizing activity, coupling activity, low flammability, ready biodegradation, non-corrosiveness, and low odor.

The fragrant composition comprises at least one fragrant compound (also referred to herein as a fragrant molecule). The fragrant molecule is also referred to as an aroma compound. The fragrant molecule can be a naturally occurring molecule or a synthetic molecule (e.g., a molecule that is synthesized in a laboratory from ingredients that are not naturally occurring). Naturally occurring molecules are those that are derived directly or indirectly from living beings (e.g., animals, plants, fruit, flowers, and the like). Naturally occurring molecules include products of naturally occurring molecules and synthetic molecules. Fragrant molecules can be found in food, wine, spices, perfumes, fragrance oils, and essential oils. For example, many form biochemically during ripening of fruits and other crops. In wines, most form as byproducts of fermentation.

Naturally occurring fragrant molecules include "essential" oils derived from plants. Essential oils are concentrated, hydrophobic liquids containing volatile fragrant molecules from plants. Essential oils are also known as volatile, ethereal oils or aetherolea, or simply as the "oil of" the plant from which they were extracted, such as, for example, oil of clove. An oil is "essential" in the sense that it carries a distinctive scent, or essence, of the plant. Essential oils do not have any specific chemical properties in common, beyond conveying characteristic fragrances. Some essential oils such as lavender, peppermint, and eucalyptus, are steam distilled. Raw plant material, comprising flowers, leaves, wood, bark, roots, seeds, or peel, are put into a distillation apparatus over water. As the water is heated the steam passes through the plant material, vaporizing the volatile compounds. The vapors flow through a coil where they condense back to liquid, which is then collected in the receiving vessel.

Essential oils are derived from berries, allspice, juniper, seeds, almond, anise, celery, cumin, nutmeg oil, bark, cassia, cinnamon, sassafras, wood, camphor, cedar, rosewood, sandalwood, agarwood, rhizome, galangal, ginger, leaves, basil, bay leaf, cinnamon, common sage, eucalyptus, lemon grass, melaleuca, oregano, patchouli, peppermint, pine, rosemary, spearmint, tea tree, thyme, wintergreen, resin, frankincense, myrrh, flowers, *cannabis*, chamomile, clary sage, clove, scented geranium, hops, hyssop, jasmine, lavender, manuka, marjoram, rose, rosemary, basil, lemon grass, ylang-ylang, peel, bergamot, grapefruit, lemon, lime, orange, tangerine, root, valerian, mango, or the like, or a combination comprising at least one of the foregoing.

Examples of fragrant molecules are alcohols (e.g., furaneol (strawberry), 1-hexanol (herbaceous, woody), cis-3-hexen-1-ol (fresh cut grass), menthol (peppermint), or the like, or a combination comprising at least one of the foregoing alcohols); aldehydes (e.g., acetaldehyde (pungent), hexanal (green, grassy), cis-3-hexenal (green tomatoes), furfural (burnt oats), or the like, or a combination comprising at least one of the foregoing aldehydes); esters (e.g., fructose (fruity, apple-like), hexyl acetate (apple, floral, fruity), ethyl methylphenylglycidate (strawberry), methyl formate, methyl acetate, methyl butyrate, methyl butanoate, ethyl acetate, ethyl butyrate, ethyl butanoate, isoamyl acetate, pentyl butyrate, pentyl butanoate, pentyl pentanoate, benzoin (extracted from resin of *styrax benzoin* tree); black pepper (from the plant piper nigrum of the piperaceae family), cajuput oil (from melaleuca cajuputi), caraway, carrot seed, coriander, cypress, dill, fennel, helichyrsum, lavandin, lemon verena, bee balm (lemon balm essential oil extracted from *melissa officinalis* of the labiatae family), niaouli, palmarosa, petitgrain, tagetes, vetiver, or the like, or a combination comprising at least one of the foregoing esters); ketones (e.g., dihydrojasmone (fruity woody floral), oct-1-en-3-one (blood, metallic, mushroom-like), 2-acetyl-1-pyrroline (fresh bread, jasmine rice), 6-acetyl-2,3,4,5-tetrahydropyridine (fresh bread, tortillas, popcorn), or the like, or a combination comprising at least one of the foregoing ketones); lactones (γ-decalactone (intense peach flavor), γ-nonalactone (coconut odor, popular in suntan lotions), δ-octalactone (creamy note, jasmine lactone powerful fatty fruity peach and apricot) massoia lactone (powerful creamy coconut, wine lactone sweet coconut odor) sotolon (maple syrup, curry, fenugreek), or the like, or a combination comprising at least one of the foregoing lactones); thiols (ethanethiol (commonly called ethyl mercaptan), grapefruit mercaptan (grapefruit), methanethiol (commonly called methyl mercaptan), 2-methyl-2-propanethiol (commonly called tertiary-butyl mercaptan)); linear terpenes (e.g., myrcene (woody, complex), geraniol (rose, flowery) nerol (sweet rose, flowery), citral, lemonal, geranial, neral (lemon, lemon myrtle, lemongrass), citronellal (lemon, lemongrass), citronellol (lemon, lemongrass, rose, pelargonium), linalool (floral, sweet, woody, lavender), nerolidol (woody, fresh bark), or the like, or a combination comprising at least one of the foregoing linear terpenes; cyclic terpenes (e.g., limonene, camphor, terpincol, ionone, thujuon, or the like, or a combination comprising at least one of the foregoing cyclic terpenes); aromatic species (e.g., benzaldehyde, eugenol, cinnamaldehyde, ethyl maltol, vanillin, anisole, anethole, estragole, thymol, or the like or a combination comprising at least one of the foregoing aromatic species); amines (e.g., thiethylamine, trimethylamine, cadaverine, pyridine, indole, skatole, or the like, or a combination comprising at least one of the foregoing amines) or the like, or a combination comprising at least one of the foregoing fragrant molecules.

Additional examples of fragrant molecules are geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzyl carbinol, trichloromethylphenylcarbinyl acetate, p-tert-butyl-cyclohexyl acetate, isononyl acetate, vetiveryl acetate, vetiverol, alpha-n-amylcinammic aldehyde, alpha-hexylcinammic aldehyde, 2-methyl-3-(p-tert-butylphenyl)-propanol, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyletetrahydropyran, methyl-dihydrojasmonate, 2-n-heptylcyclopentanone, 3-methyl-2-pentylcyclopentanone, n-decanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphycyclohexanol, cedryl methyl ether, isolongifolanone, aubepine nitrile, aubepine, heliotropine, coumarin, eugenol, vanillin, diphenyl oxide, hydroxycitronellal, ionones, methylionones, isomethylioniones, irones, cis-3-hexenol and esters thereof, indane musk, tetralin musk, isochroman musk, macrocyclic ketones, macrolactone musk, ethylene brassylate, aromatic nitromusk.

Exemplary fragrant molecules include bergamot oil, coriander oil, dimethyl heptanol, dimethyl benzyl carbinyl acetate, geranyl acetate, citronellyl acetate, rose synthetic, geranium bourbon, hedione, iso eugenol, methyl eugenol styrallyl acetate, stemone, rose oxide laevo, aldehyde C-11 undecyclic, derivatives of 2,6-dimethyl-2-alkoxy octan-7-ol, vertivert oil, vetiverol, vetiveryl, acetate, quaiac wood oil, esters ol-anthranilic acid, benzyl salicylate, benzyl benzoate, oak moss, eugenol, p-tert-butyl cyclohexyl acetate and coumarin.

In one embodiment, an additional solvent may be used in the fragrant formulation in addition to the alkyl ketal ester. Polar solvents such as water, propylene carbonate, ethylene carbonate, butyrolactone, acetonitrile, benzonitrile, nitromethane, nitrobenzene, sulfolane, dimethylformamide, N-methylpyrrolidone, glycol ethers, methyl acetate, ethyl acetate, methanol, acetonitrile, nitromethane, ethanol, propanol, isopropanol, butanol, benzyl alcohol, butoxydiglycol, 1,2-propane diol (propylene glycol), 1,3-propane diol, ethoxydiglycol, hexylene glycol, and dipropylene glycol, triethylene glycol, hexylene glycol, diethylene glycol, ethylene glycol, propylene glycol, 1,2-butylene glycol or the like, or combinations comprising at least one of the foregoing solvents are generally desirable. Non-polar solvents such a benzene, toluene, methylene chloride, carbon tetrachloride, hexane, diethyl ether, hexane, tetrahydrofuran, or the like, or combinations comprising at least one of the foregoing non-polar solvents may also be used. Co-solvents comprising at least one polar solvent and at least one non-polar solvent may also be utilized to modify the compatibilizing capabilities of the solvent and thereby adjust the clarity and haze characteristics of the fragrant formulation. Exemplary solvents are methyl acetate, ethyl acetate, glycol ethers and water. Glycol ethers and alcohols can be used to compatibilize the alkyl ketal ester with water if desired. Exemplary solvents are water and ethyl alcohol.

In one embodiment, the fragrant formulation can optionally comprise a radical scavenger or a source of a radical scavenger. As used herein the term radical scavenger refers to a species that can react with a carbonate radical to convert the carbonate radical by a series of fast reactions to a less reactive species, i.e. a carbonate radical scavenger.

Radical scavengers can be selected from the classes of alkanolamines, amino sugars, amino acids, esters of amino acids and mixtures thereof. For example, the following compounds can be employed as radical scavengers: ethylamine, monoethanolamine, 2-methoxyethylamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, morpholine, piperidine, or the like, or a combination comprising at least one of the foregoing radical scavengers.

The fragrant formulation can optionally comprise a polymer. It is generally desirable for the polymer to be soluble in the alkyl ketal ester and/or in the cosolvent used with the alkyl ketal ester. In one embodiment, the polymer is water-soluble. In another embodiment, the polymer is not water-soluble and exists as a dispersion in the fragrant formulation.

It is desirable for the polymer to be an organic polymer. The polymer may be a thermoplastic, a thermosetting polymer, or a combination of a thermosetting polymer with a thermoplastic polymer. In one embodiment, the polymer may be an oligomer, a homopolymer or a copolymer. The copolymer can be a block copolymer, a star block copolymer, a random copolymer, an alternating block copolymer, a dendrimer, an ionic block copolymer, a polyelectrolyte, or the like, or a combination comprising at least one of the foregoing polymer.

Examples of polymers that are water-soluble are polyvinyl alcohol, polyacrylamides, polyvinylpyrrollidones, polyamides, hydroxyalkyl celluloses such as hydroxyethylcellulose and hydroxypropylcellulose, polyacrylic acid, or the like, or a combination comprising at least one of the foregoing water-soluble polymers.

Examples of polymers that are not water-soluble are polymethylmethacrylates, polyacrylates, polyesters, polyimides, polyethers, polyolefins, polyetherketones, polyether ether ketones, polyether ketone ketones, polycarbonates, polyarylene ethers, epoxies, polysulfones, polyethersulfones, polyetherimides, polynorbornylene, polysiloxanes, polyvinylchlorides, fluoropolymers, liquid crystalline polymers, ionomers, or the like, or combinations comprising at least one of the foregoing non-water-soluble polymers.

The polymers can be used as rheology modifiers, dispersants, stabilizers, promoters, or antimicrobials, and the like; in industrial product applications, such as, textiles (processing, finishing, printing, and dyeing aids, protective washable surface coatings, manufacture of synthetic leather by saturation of non-woven fabrics, and the like; manufacturing of woven fabrics, non-woven fabrics, natural and synthetic fibers and the like); water treatments (waste water, cooling water, potable water purification, and the like); chemical spill containments (acid-spill absorbent, and the like); leather and hide processing (processing aids, finishing, coating, embossing, and the like); paper and papermaking (surface coatings, such as pigmented coatings, antistatic coatings, and the like, pulp binders, surface sizings, dry and wet strength enhancers, manufacture of wet-laid felts, and the like); printing (inks, antiwicking ink-jet printer inks, thickeners for ink formulations containing cationic dyes for printing acrylic fabrics, and the like); paints (pigment and grinding additive, crosslinking agent for epoxy latex emulsions, particulate-suspending aid for clays, pigments, and the like); industrial plant effluent treatment (flocculants for phenolics in paper mill effluent, and the like); metal working (acid etch cleaners, low pH metal coatings, pickling agents in cold rolled steel processing, and the like); adhesives (clear adhesives, adhesion promoters for metal, plastic, wood, and the like, non-woven floc adhesive tie coatings, bonding, and the like); wood preservation; and industrial construction products for buildings and roads (cement plasticizers, asphalt emulsion stabilizers at low pH, acid etch for cement, consistency modifiers of concrete, mortar, putty, and the like).

The polymer has a number average molecular weight of less than or equal to about 1,000,000 grams per mole, specifically less than or equal to about 500,000 grams per mole, specifically less than or equal to about 50,000 grams per mole, and more specifically less than or equal to about 5,000 grams per mole.

Other additives may also be added to the fragrant composition to form a fragrant formulation. These additives are optional. Suitable additives are antioxidants, antiozonants, antibacterial agents, humectants, colorants, dyes, pigments, food additives, pheromones, musks, a carbonate ion source, an alkalizing agent, a pH buffer, a conditioning agent, a chelant, an auxiliary agent, solvents (e.g., a cosolvent), surfactants (as cleansing agents, emulsifying agents, foam boosters, hydrotropes, solubilizing agents, and suspending agents), nonsurfactant suspending agents, emulsifiers, skin conditioning agents (emollients, humectants, moisturizers, and the like), hair conditioning agents, hair fixatives, film-formers, skin protectants, binders, chelating agents, antimicrobial agents, antifungal agents, antidandruff agents, abrasives, adhesives, absorbents, dyes, deodorant agents, antiperspirant agents, opacifying and pearlescing agents, preservatives, propellants, spreading aids, sunscreen agents, sunless skin tanning accelerators, ultraviolet light absorbers, pH adjusting agents, botanicals, hair colorants, oxidizing agents, reducing agents, skin bleaching agents, pigments, physiologically active agents, anti-inflammatory agents, topical anesthetics, fragrance and fragrance solubilizers, a polymer, and the like, in addition to ingredients previously discussed that may not appear herein. Oral care products, for example, can contain anticaries, antitartar and/or antiplaque agents in addition to surfactants, abrasives, humectants, flavorants, or the like, or a combination comprising at least one of the foregoing additives.

In one embodiment, in one method of manufacturing the fragrant formulation, a fragrant composition an alkyl ketal ester as described above, an optional solvent, an optional active agent, an optional surfactant, an optional thickening agent, an optional compatibilizer and desired additives are blended together in the desired quantities in a reactor. The reactor may be a batch or continuous reactor. It is desirable for the reactor to be fitted with a mechanism for agitating the fragrant formulation. The fragrant formulation may be heated if desired to evaporate some solvent or to further drive compatibilization between the fragrant composition, the alkyl ketal ester and the optional solvent.

In another embodiment, in another method of manufacturing the fragrant formulation, the alkyl ketal ester may be used as an extraction solvent to extract a fragrant composition such as essential oils from naturally occurring substances. The alkyl ketal ester may be retained with the essential oil and further processed to form a desired fragrant formulation. The essential oils can be extracted via steam extraction, supercritical extraction or solvent extraction. An alkyl ketal ester can be used in conjunction with steam, supercritical solvents or normal solvents (solvents that are not in a supercritical state) to effect extraction of essential oils. An alkyl ketal ester can also be used by itself to extract essential oils.

Steam extraction is normally environmentally friendly and uses only water to effect the extraction. Water is not however, a good solvent for all essential oils. An alkyl ketal ester can be used in conjunction with water to extract additional essential oil from a naturally occurring substance than that which would be extracted by using only steam for the extraction. The use of the alkyl ketal ester in steam extraction would continue to render the process environmentally friendly, while at the same time being effective to extract additional oil from the naturally occurring substance.

Supercritical extraction is generally conducted with carbon dioxide, but can also be effected with other solvents. A blend of supercritical carbon dioxide and an alkyl ketal ester can be used to extract essential oils for the fragrant formulation. Liquid carbon dioxide (that is not in a supercritical state) blended with alkyl ketal esters can also be used for extraction. Other supercritical fluids can also be blended with alkyl ketal esters to extract essential oils.

Hexane extraction is generally used to extract a variety of essential oils. An alkyl ketal ester can be blended with the hexane (or other solvents) to facilitate improved extraction. Ethanol is often used to target the segregation of a target molecule from hexane after extraction. In one embodiment, while the alkyl ketal ester is used to facilitate the extraction of an essential oil in conjunction with hexane, it can also be used to facilitate a segregation of a target molecule from the hexane. By changing the ratio of the amount of the alkyl ketal ester in the mixture of the target molecule and hexane and/or temperature, the target molecule can be segregated after the extraction. Other solvents can be used in conjunction with the alkyl ketal ester to facilitate segregation of the target molecule.

In yet another embodiment, the alkyl ketal ester by itself can be used to facilitate an extraction of various essential oils from naturally occurring substances. The alkyl ketal ester can be blended with the naturally occurring substance and under suitable combinations of temperature and pressure can facilitate the extraction of an essential oil from the naturally occurring substance. The resulting product can then be subjected to purification processes such as filtration, decantation, distillation, and the like to obtain a purified mixture of the essential oil and the alkyl ketal ester. The mixture of the essential oil and the alkyl ketal ester can then be blended with other suitable ingredients to produce the desired fragrant formulation. Thus the alkyl ketal ester may be used not only to extract the essential oil but can serve as a solubilizing solvent and/or a fixative in the fragrant formulation.

The blending to form the fragrant composition or the fragrant formulation may be conducted via dry blending, melt blending, solution blending or a combination comprising at least one of the foregoing forms of blending. Dry blending encompasses blending without the use of solvents and is generally conducted to blend two or more fragrant compositions. Melt blending occurs when the temperature of blending is conducted above the melting point of some of the ingredients and wet blending is generally conducted in the presence of solvents.

The blending of the formulation involves the use of shear force, extensional force, compressive force, ultrasonic energy, electromagnetic energy, thermal energy or combinations comprising at least one of the foregoing forces or forms of energy and is conducted in processing equipment wherein the aforementioned forces are exerted by a single screw, multiple screws, intermeshing co-rotating or counter rotating screws, non-intermeshing co-rotating or counter rotating screws, reciprocating screws, screws with pins, barrels with pins, rolls, rams, helical rotors, or combinations comprising at least one of the foregoing.

Blending involving the aforementioned forces may be conducted in machines such as single or multiple screw extruders, Buss kneader, Henschel, helicones, Ross mixer, Banbury, roll mills, molding machines such as injection molding machines, vacuum forming machines, blow molding machine, kettles, kettles with distillation and/or condensation columns, or then like, or combinations comprising at least one of the foregoing machines.

The fragrant formulation may be used in a variety of articles and applications. It may be used in body lotions, shampoos, massage oils, as a chemical identifier (e.g., in non-smelling chemicals or in toxic or hazardous chemicals), to mask odor, in perfume sticks and lanterns, air fresheners, candles, paints, varnishes, furniture, insect repellents, in polymers, cleaners, detergents, cosmetics, toiletries, cosmeceuticals and beauty aids, personal hygiene and cleansing products applied to the skin, hair, scalp, and nails of humans and animals. The fragrant formulations are used in a variety of air fresheners such as for example, spray, gel (e.g., an electric air freshener or beads), a paper substrate (e.g., car air fresheners hanging from rearview mirrors) or liquid (e.g., reed diffusers or with electric air fresheners).

The term "health care products" as used herein includes pharmaceuticals, pharmacosmetics, oral care products (mouth, teeth), eye care products, ear care products and over-the-counter products and appliances, such as patches, plasters, dressings and the like, and medical devices externally applied to or into the body of humans and animals for ameliorating a health-related or medical condition, for generally maintaining hygiene or well-being, and the like. The term "body" includes the keratinous (hair, nails) and non-keratinous skin areas of the entire body (face, trunk, limbs, hands and feet), the tissues of body openings and eyes, and the term "skin" includes the scalp and mucous membranes. The term "household care products" as used herein includes products employed in a domestic household for surface cleaning, odor control or masking, or biocidal cleaning products for maintaining sanitary conditions, such as in the kitchen and bathroom, laundry products for fabric care and cleaning, air fresheners, air sanitizers, air deodorizers/odor removers, candles, and the like. These products can be used in the home, in the workplace, or in institutional settings.

The fragrant composition or fragrant formulation is generally added as a concentrate to an article to produce a desired sensory effect in the article. The ratio of the fragrant composition to the alkyl ketal ester used in the fragrant formulation may vary from article to article depending upon the composition of the article. In addition, the amount of the fragrant composition may also vary from article to article depending upon the utility of the article.

In one embodiment, the fragrant formulation may be added to organic polymer formulations to impart to the organic polymer a particular odor or in order to mask an undesirable odor. Examples of polymers to which the fragrant formulation can be added are polyolefins, polyvinyl acetates, polystyrenes cellulose acetates, acrylonitrile butadiene styrene, polyacrylics, polycarbonates, polyamides, polyurethanes, epoxies, and polyesters.

The following examples, which are not meant to be limiting, demonstrate some of the compositions and formulations and the methods disclosed herein.

EXAMPLES

Ex. #s 1-44

The following examples were conducted to demonstrate soluble formulations that included an alkyl ketal ester and an essential oil.

Table 1 shows 44 different fragrant formulations (Sample #s 1-44) that were obtained by blending an alkyl ketal ester and an essential oil. The alkyl ketal ester and the essential oil were blended in a weight ratio of 1:1 at room temperature using gentle agitation. Solubility was visually determined immediately after mixing. Clear solutions are described as "miscible" and solutions that are either cloudy or show evidence of a second phase are labeled as "immiscible." Et-LGK is an abbreviation for the glycerol ketal of ethyl levulinate while Et-LPK is an abbreviation for the propylene glycol ketal of ethyl levulinate, both of which are alkyl ketal esters. Bu-LGK is an abbreviation for the glycerol ketal of butyl levulinate.

TABLE 1

| Ex. # | Solvent | Pure Essential Oil | Miscibility of 50/50 blend by weight |
|---|---|---|---|
| 1 | Et-LGK | Orange (*Citrus sinensis*) | Miscible |
| 2 | Et-LGK | Patchouli (*Pogostemon patchouli*) | Miscible |
| 3 | Et-LGK | Ylang ylang (*Canaga odorata*) | Miscible |
| 4 | Et-LGK | Coriander seed (*Coriandrum sativum*) | Miscible |
| 5 | Et-LGK | Birch sweet (*Betula lenta*) | Miscible |
| 6 | Et-LGK | Cedarwood (*Cedrus atlantica*) | Miscible |
| 7 | Et-LGK | Citronella (*Cymbopogon nardus*) | Miscible |
| 8 | Et-LGK | Pine needle (*pinus sylvestris*) | Miscible |
| 9 | Et-LGK | Vetiver (*Vetivera zizanoides*) | Miscible |
| 10 | Et-LGK | Basil (*Ocimum basilicum*) | Miscible |
| 11 | Et-LGK | Myrrh (*Commiphora myrrha*) | Miscible |
| 12 | Et-LGK | Geranium (*Pelargonium graveolens*) | Miscible |
| 13 | Et-LGK | Bergamot (*Citrus bergamia*) | Miscible |
| 14 | Et-LGK | Lavender (*Lavandula angustifolium*) | Miscible |
| 15 | Et-LPK | Orange (*Citrus sinensis*) | Miscible |
| 16 | Et-LPK | Patchouli (*Pogostemon patchouli*) | Miscible |
| 17 | Et-LPK | Ylang ylang (*Canaga odorata*) | Miscible |
| 18 | Et-LPK | Coriander seed (*Coriandrum sativum*) | Miscible |
| 19 | Et-LPK | Birch sweet (*Betula lenta*) | Miscible |
| 20 | Et-LPK | Citronella (*Cymbopogon nardus*) | Miscible |
| 21 | Et-LPK | Pine needle (*pinus sylvestris*) | Miscible |
| 22 | Et-LPK | Vetiver (*Vetivera zizanoides*) | Miscible |
| 23 | Et-LPK | Basil (*Ocimum basilicum*) | Miscible |
| 24 | Et-LPK | Myrrh (*Commiphora myrrha*) | Miscible |
| 25 | Et-LPK | Geranium (*Pelargonium graveolens*) | Miscible |
| 26 | Et-LPK | Bergamot (*Citrus bergamia*) | Miscible |
| 27 | Et-LPK | Lavender (*Lavandula angustifolium*) | Miscible |
| 28 | Bu-LGK | Orange (*Citrus sinensis*) | Miscible |
| 29 | Bu-LGK | Patchouli (*Pogostemon patchouli*) | Miscible |
| 30 | Bu-LGK | Ylang ylang (*Canaga odorata*) | Miscible |
| 31 | Bu-LGK | Coriander seed (*Coriandrum sativum*) | Miscible |
| 32 | Bu-LGK | Birch sweet (*Betula lenta*) | Miscible |
| 33 | Bu-LGK | Citronella (*Cymbopogon nardus*) | Miscible |
| 34 | Bu-LGK | Pine needle (*pinus sylvestris*) | Miscible |
| 35 | Bu-LGK | Vetiver (*Vetivera zizanoides*) | Miscible |
| 36 | Bu-LGK | Basil (*Ocimum basilicum*) | Miscible |
| 37 | Bu-LGK | Myrrh (*Commiphora myrrha*) | Miscible |
| 38 | Bu-LGK | Geranium (*Pelargonium graveolens*) | Miscible |
| 39 | Bu-LGK | Bergamot (*Citrus bergamia*) | Miscible |
| 40 | Bu-LGK | Lavender (*Lavandula angustifolium*) | Miscible |
| 41 | Et-LPK | Cinnamon oil | Miscible |
| 42 | Et-LPK | Eucalyptus oil | Miscible |
| 43 | Et-LGK | Cinnamon oil | Miscible |
| 44 | Et-LGK | Eucalyptus oil | Miscible |

Examples 45-57

These examples were conducted to demonstrate the compatibilizing capabilities of alkyl ketal esters to obtain the fragrant formulations. Table 2 shows 7 compositions (Sample #s 45-51) that contained the alkyl ketal ester, water and the essential oil. The respective weight percentages for each ingredient are shown in Table 2 along with whether the ingredients are miscible or immiscible. Table 4 details the comparative compositions (Sample #s 52-57) that contain ethanol. In both Tables 2 and 4, the ingredients were added at room temperature and gently agitated by shaking. Solubility was visually determined immediately after mixing. Clear solutions are described as "miscible" and solutions that are either cloudy or show evidence of a second phase are labeled as "immiscible." The compositions for the oil blend A are shown in the Table 3 below.

TABLE 2

| Ex. # | Essential Oil | Weight % Et-LGK | Weight % of Essential Oil | Weight % of water | Miscibility of Blend |
|---|---|---|---|---|---|
| 45 | Patchouli (*Pogostemon patchouli*) | 50 | 50 | 0 | Miscible |
| 46 | Patchouli (*Pogostemon patchouli*) | 44.1 | 44.1 | 11.8 | Immiscible |
| 47 | Patchouli (*Pogostemon patchouli*) | 75.4 | 19.4 | 5.2 | Immiscible |
| 48 | Patchouli (*Pogostemon patchouli*) | 83.7 | 12.9 | 3.4 | Miscible |
| 49 | Oil Blend A* | 0 | 13.7 | 86.3 | Immiscible |
| 50 | Oil Blend A* | 52.9 | 6.4 | 40.7 | Immiscible |
| 51 | Oil Blend A* | 63.7 | 5 | 31.4 | Miscible |

TABLE 3

| Weight % | Essential Oil |
|---|---|
| 5.9% | lavender |
| 5.9% | orange |
| 7.5% | vetiver |
| 7.9% | myrrh |
| 6.3% | coriander seed |
| 5.7% | geranium |
| 6.1% | ylang ylang |
| 6.8% | basil |

TABLE 3-continued

| Weight % | Essential Oil |
|---|---|
| 6.1% | pine needle |
| 12.0% | patchouli |
| 5.7% | citronella |
| 9.3% | cedarwood |
| 9.5% | birch sweet |
| 5.2% | bergamot |

TABLE 4

| Comp. Ex. # | Essential Oil | Weight % Ethanol | Weight % of Essential Oil | Weight % of water | Miscibility of Blend |
|---|---|---|---|---|---|
| 52 | Patchouli (*Pogostemon patchouli*) | 50 | 50 | 0 | Miscible |
| 53 | Patchouli (*Pogostemon patchouli*) | 42.2 | 43.6 | 14.2 | Immiscible |
| 54 | Patchouli (*Pogostemon patchouli*) | 59.6 | 30.4 | 10 | Immiscible |
| 55 | Patchouli (*Pogostemon patchouli*) | 64.9 | 26.5 | 8.7 | Miscible |
| 56 | Oil Blend A | 0 | 13.7 | 86.3 | Immiscible |
| 57 | Oil Blend A | 45 | 7.5 | 47.5 | Miscible |

From the examples above, it may be seen that the alkyl ketal esters can be effectively used in fragrant formulations to solvate essential oils. The alkyl ketal esters can be used in the fragrant formulations in amounts of about 40 to about 80 wt %, and specifically about 50 to about 70 wt %, based on the total weight of the fragrant formulation.

Examples 58-111

The following examples demonstrate compatibility or incompatibility between various fragrant compositions and the alkyl ketal esters. Table 5 demonstrates the solubility of Et-LGK with the oils listed. Table 6 demonstrates the solubility of Bu-LGK with the listed oils, while Table 7 demonstrates the solubility of Et-LPK with the listed oils.

TABLE 5

| Example # | Oil | % alkyl ketal ester | Result |
|---|---|---|---|
| 58 | Castor oil | 50 | miscible |
| 59 | C12-15 alkyl benzoate | 50 | miscible |
| 60 | Isopropyl myristate | 50 | miscible |
| 61 | Caprylic/capric triglycerides | 50 | miscible |
| 62 | Octyl palmitate | 25 | immiscible |
| 63 | Octyl palmitate | 10 | miscible |
| 64 | Mineral oil | 25 | immiscible |
| 65 | Safflower Oil | 25 | immiscible |
| 66 | Coconut Oil | 50 | immiscible |
| 67 | cyclomethicone | 10 | immiscible |
| 68 | Avocado oil | 50 | immiscible |
| 69 | Avocado oil | 10 | miscible |
| 70 | Canola oil | 25 | miscible |
| 71 | Grapeseed Oil | 25 | immiscible |
| 72 | Grapeseed Oil | 10 | miscible |
| 73 | Sesame seed oil | 10 | immiscible |
| 74 | Soybean oil | 10 | miscible |
| 75 | Squalane Pripure 3759 | 10 | immiscible |
| 76 | Caprylyl methicone (DC FZ-3196) | 11 | immiscible |
| 77 | Oleyl alcohol | 50 | miscible |

TABLE 6

| Example | Oil | % alkyl ketal ester | Result |
|---|---|---|---|
| 78 | Castor oil | 50 | miscible |
| 79 | C12-15 alkyl benzoate | 25 | miscible |
| 80 | Isopropyl myristate | 25 | miscible |
| 81 | Caprylic/capric triglycerides | 50 | miscible (prophetic) |
| 82 | Octyl palmitate | 25 | miscible |
| 83 | Mineral oil | 10 | immiscible |
| 84 | Safflower Oil | 25 | miscible |
| 85 | Coconut Oil | 50 | miscible |
| 86 | cyclomethicone | 10 | immiscible |
| 87 | Avocado oil | 50 | miscible |
| 88 | Canola oil | 50 | miscible |
| 89 | Grapeseed Oil | 50 | miscible |
| 90 | Sesame seed oil | 50 | miscible |
| 91 | Soybean oil | 53 | miscible |
| 92 | Soybean oil | 13 | miscible |
| 93 | Squalane Pripure 3759 | 10 | immiscible |
| 94 | Caprylyl methicone (DC FZ-3196) | 10 | immiscible |
| 95 | Oleyl alcohol | 50 | miscible |

TABLE 7

| Example | Oil | % alkyl ketal ester | Result |
|---|---|---|---|
| 96 | Castor oil | 50 | Miscible |
| 97 | C12-15 alkyl benzoate | 25 | Miscible (prophetic) |
| 98 | Isopropyl myristate | 50 | Miscible |
| 99 | Caprylic/capric triglycerides (Neobee M-5) | 50 | Miscible |
| 100 | Octyl palmitate | 50 | Miscible |
| 101 | Mineral oil | 50 | Miscible |
| 102 | Coconut Oil | 50 | miscible |
| 103 | cyclomethicone | 50 | miscible |
| 104 | Avocado oil | 50 | miscible |
| 105 | Canola oil | 50 | miscible |
| 106 | Grapeseed Oil | 50 | miscible |
| 107 | Sesame seed oil | 29 | miscible |
| 108 | Soybean oil | 49 | miscible |
| 109 | Squalane Pripure 3759 | 50 | miscible |
| 110 | Caprylyl methicone (DC FZ-3196) | 50 | miscible |
| 111 | Oleyl alcohol | 50 | miscible |

From the Tables 5-7 above, it may be seen that materials including vegetable oils, animal fats and derivatives are useful fragrant compounds and can be miscible with at least one of the alkyl ketal esters. Examples of useful fragrant compounds include for example, acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, *macadamia* nut oil, rose hip oil, ajwain oil, angelic root oil, anise oil, aragan oil, asafetida, balsam oil, basil oil, bay oil, bergamot oil, black pepper essential oil, buchu oil, birch oil, camphor, *cannabis* oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

Oils which have a required HLB of at least 6, or at least 7, at least 8 or at least 10, tend to dissolve more easily in the alkyl ketal esters and are preferred in cases in which the alkyl ketal ester is to reside at least partially in an oil phase, or in which the alkyl ketal ester is to dissolve or be dissolved into the oil.

Examples 112-114

These examples demonstrate the manufacturing of perfume formulations that contain alkyl ketal esters. Table 8 reflects Examples 112-114. Components were added at room temperature and gently agitated by shaking. Solubility was visually determined immediately after mixing. All formulations were clear. Composition is given in weight percent (wt %).

TABLE 8

|  | Example 58 | Example 59 | Example 60 |
| --- | --- | --- | --- |
| orange oil | 1.1% | 1.4% | 1.3% |
| bergamot | 1.2% | 1.9% | 1.8% |
| myrrh | 1.4% | 1.2% | 1.1% |
| citronella | 1.0% | 1.3% | 1.2% |
| cedarwood | 0.7% | 0.6% | 0.6% |
| DI water | 28.5% | 8.2% | 14.7% |
| Et-LGK | 7.1% | 0 | 0 |
| Et-LPK | 0 | 6.6% | 6.1% |
| ethanol | 59.1% | 78.9% | 73.2% |

Example 115

This is a prophetic example that describes the manufacturing of an air freshener. The formulation is listed in Table 9 below. In order to manufacture the air freshener, the ingredients of part A and part B are first mixed individually and then added together with continual mixing. The ingredients of Part A are added in the order listed in the Table 9 and then mixed for a minimum for a period of 30 minutes. The water is heated to 100-130° F.

TABLE 9

| Ingredient | Weight % |
| --- | --- |
| Part A | |
| DI Water | 65.7 |
| Laponite RD | 3.0 |
| Aqualon CMC-9H4F | 0.3 |
| Part B | |
| Ketal | 15 |
| Fragrance | 15 |
| Cola ® Mulse Emultron PM | 1 |

Examples 116-125

The following examples were conducted to demonstrate the use of a fragrant formulation in candles. Compatibility between various waxes and the alkyl ketal esters was first determined as detailed below. Table 10 below details the fragrant formulations for 10 different candles (Examples 116-125) that contain the fragrant composition.

Beeswax

Beeswax and Et-LGK were weighed into a vessel in a 50/50 weight ratio and heated to 80° C. to form a uniform molten mixture. Two layers formed upon cooling to room temperature. At 25/75 weight ratio of Et-LGK to beeswax, a uniform liquid mixture formed at 80° C. and a single homogenous wax layer formed upon cooling.

Beeswax and Bu-LGK were weighed into a vessel at 50/50 weight ratio and heated to 80° C. to form a uniform molten mixture. The mixture formed a single homogenous wax layer upon cooling to room temperature.

Beeswax and Et-LPK were weighed into a vessel at 50/50 weight ratio and heated to 80° C. to form a uniform molten mixture. The mixture formed a single homogenous wax layer upon cooling to room temperature.

Paraffin Wax

Paraffin wax and Et-LGK were weighed into a vessel at 50/50 weight ratio and heated to 80° C. to form a uniform molten mixture. Two layers formed upon cooling to room temperature. Paraffin wax and Et-LGK were weighed into a vessel at 90/10 weight ratio and heated to 80° C. to form a uniform molten mixture. The mixture formed a single homogenous wax layer upon cooling to room temperature.

Paraffin wax and Bu-LGK were weighed into a vessel at 75/25 weight ratio and heated to 80° C. to form a uniform molten mixture. Two layers formed upon cooling to room temperature.

Paraffin wax and Et-LPK were weighed into a vessel at 50/50 weight ratio and heated to 80° C. to form a uniform molten mixture. The mixture formed a single homogenous wax layer upon cooling to room temperature. Paraffin wax and Et-LPK were weighed into a vessel at 75/25 weight ratio and heated to 80° C. to form a uniform molten mixture. The mixture formed a single homogenous wax layer upon cooling to room temperature.

Gulf Wax brand of household paraffin wax for canning and candlemaking (distributed by Royal Oak Enterprises) was used in these experiments.

Carnauba Wax

Carnauba wax and Et-LGK were weighed into a vessel at 50/50 weight ratio and heated to 120° C. to form a uniform molten mixture. Two layers formed upon cooling to room temperature. At 75/25 weight ratio of carnauba wax to Et-LGK, a uniform liquid mixture formed at 120° C. and a single homogenous wax layer was formed upon cooling.

Carnauba wax and Bu-LGK were weighed into a vessel at 50/50 weight ratio and heated to 120° C. to form a uniform molten mixture. A single homogenous wax layer was formed upon cooling.

Carnauba wax and Et-LPK were weighed into a vessel at 50/50 weight ratio and heated to 120° C. to form a uniform molten mixture. A single homogenous wax layer was formed upon cooling.

Candelilla Wax

Candelilla wax and Et-LGK were weighed into a vessel at 75/25 weight ratio and heated to 120° C. to form a uniform molten mixture. Two layers formed upon cooling to room temperature. At 90/10 weight ratio of candelilla wax to Et-LGK, a uniform liquid mixture formed at 120° C. and a single homogenous wax layer was formed upon cooling.

Candelilla wax and Bu-LGK were weighed into a vessel at 50/50 weight ratio and heated to 120° C. to form a uniform molten mixture. A single homogenous wax layer was formed upon cooling.

Candelilla wax and Et-LPK were weighed into a vessel at 50/50 weight ratio and heated to 120° C. to form a uniform molten mixture. A single homogenous wax layer was formed upon cooling.

NatureWax P-1

NatureWax P-1 and Et-LGK were weighed into a vessel at 75/25 weight ratio and heated to 80° C. to form a uniform molten mixture. A single homogenous wax layer was formed upon cooling.

NatureWax P-1 and Bu-LGK were weighed into a vessel at 50/50 weight ratio and heated to 80° C. to form a uniform molten mixture. A single homogenous wax layer was formed upon cooling.

NatureWax P-1 and Et-LPK were weighed into a vessel at 75/25 weight ratio and heated to 80° C. to form a uniform molten mixture. A single homogenous wax layer was formed upon cooling.

Nature Wax C-1

NatureWax C-1 and Et-LGK were weighed into a vessel at 90/10 weight ratio and heated to 80° C. to form a uniform molten mixture. A single homogenous wax layer was formed upon cooling.

NatureWax C-1 and Bu-LGK were weighed into a vessel at 50/50 weight ratio and heated to 80° C. to form a uniform molten mixture. A single homogenous wax layer was formed upon cooling.

NatureWax C-1 and Et-LPK were weighed into a vessel at 90/10 weight ratio and heated to 80° C. to form a uniform molten mixture. A single homogenous wax layer was formed upon cooling.

Nature Wax C-3

NatureWax C-3 and Et-LGK were weighed into a vessel at 90/10 weight ratio and heated to 80° C. to form a uniform molten mixture. A single homogenous soft wax layer was formed upon cooling.

NatureWax C-3 and Bu-LGK were weighed into a vessel at 90/10 weight ratio and heated to 80° C. to form a uniform molten mixture. A single homogenous wax layer was formed upon cooling.

NatureWax C-3 and Et-LPK were weighed into a vessel at 90/10 weight ratio and heated to 80° C. to form a uniform molten mixture. A single homogenous wax layer was formed upon cooling.

Stearic Acid

Stearic acid and Et-LGK were weighed into a vessel at 50/50 weight ratio and heated to 80° C. to form a uniform molten mixture. Two layers formed upon cooling to room temperature. At 25/75 Et-LGK to stearic acid by weight, a uniform liquid mixture formed at 80° C. and a single homogenous wax layer was formed upon cooling.

Stearic acid and Et-LPK were weighed into a vessel at 50/50 weight ratio and heated to 80° C. to form a uniform molten mixture. The mixture formed a single homogenous wax layer upon cooling to room temperature.

The following Table 10 details formulations for different candles that contain the waxes detailed above and the alkyl ketal ester. The formulations were manufactured by combining three parts (Part A, Part B and Part C). Candle formulations 116-120 (Examples 116-120) were manufactured by weighing Part A ingredients into a vessel and heating them at 80° C. until the mixture was in liquid from. The vessel was removed from the heat and Part C was added to the vessel. While the mixture was still liquid, the mixture was poured into a container and a wick with a metal tab base was inserted into the center of the mixture. The completed candle was allowed to cool to room temperature.

Candle formulations 121-124 (Examples 121-124) were manufactured by weighing Part A into a vessel and heated them at 80° C. until the mixture was liquid. Part B was added to Part A and mixed for 2 minutes. The vessel was removed from the heat and Part C was added to the vessel. While the mixture was still liquid, the candle was poured into a container and a wick with a metal tab base was inserted into the center of the mixture. The completed candle was allowed to cool to room temperature. Example 124 was allowed to cool to 65° C. before pouring into the candle mold. Examples 121-124 were poured into small tea light candle sizes.

Candle formulation 125 was manufactured by weighing the ingredients for Part B. Part B was mixed by hand and set aside. Part A ingredients were weighed into a vessel and heated at 80° C. until the mixture was in liquid from. The pre-mix of Part B was added to Part A and mixed together for 2 minutes. The vessel containing Part A and Part B was removed from the heat and Part C was added. The mixture was cooled to 65° C. and then poured into a container and a wick with a metal tab base was inserted into the center of the mixture. The completed candle was allowed to cool to room temperature.

TABLE 7

| Ingredient | 116 | 117 | 118 | 119 | 120 | 121 | 122 | 123 | 124 | 125 |
|---|---|---|---|---|---|---|---|---|---|---|
| Part A (ingredient weights given as weight % of total formulation) | | | | | | | | | | |
| Nature Wax P-1 | 22.5% | 10% | 28% | 28% | 28% | 0% | 0% | 0% | 0% | 0% |
| Nature Wax C-1 | 22.5% | 26% | 6% | 6% | 6% | 29.9% | 29.9% | 29.9% | 29.9% | 31.5% |
| Nature Wax C-3 | 22.5% | 26% | 0% | 0% | 0% | 29.9% | 29.9% | 29.9% | 29.9% | 31.5% |
| Beeswax | 22.5% | 28% | 56% | 56% | 56% | 29.9% | 29.9% | 29.9% | 29.9% | 31.5% |

TABLE 7-continued

| Ingredient | 116 | 117 | 118 | 119 | 120 | 121 | 122 | 123 | 124 | 125 |
|---|---|---|---|---|---|---|---|---|---|---|
| Part B (ingredient weights given as weight % of total formulation) | | | | | | | | | | |
| Cinqasia Red B RT-195-1 | 0% | 0% | 0% | 0% | 0% | 0.23% | 0.23% | 0.23% | 0.23% | 0.24% |
| Et-LGK | 0% | 0% | 0% | 0% | 0% | 0% | 0% | 0% | 0% | 5.25% |
| Part C (ingredient weights given as weight % of total formulation) | | | | | | | | | | |
| Et-LGK | 0% | 0% | 5% | 0% | 0% | 4.99% | 0% | 0% | 0% | 0% |
| Bu-LGK | 5% | 5% | 0% | 0% | 5% | 0% | 0% | 4.99% | 4.99% | 0% |
| Et-LPK | 0% | 0% | 0% | 5% | 0% | 0% | 4.99% | 0% | 0% | 0% |
| Bergamot (*Citrus bergamia*) essential oil | 5% | | 5% | 5% | 5% | 0% | 0% | 0% | 0% | 0% |
| Grapefruit essential oil | 0% | 4% | 0% | 0% | 0% | 0% | 0% | 0% | 0% | 0% |
| Lavender (*Lavandula angustifolium*) essential oil | 0% | 1% | 0% | 0% | 0% | 0% | 0% | 0% | 0% | 0% |
| Lemon essential oil | 0% | 0% | 0% | 0% | 0% | 4.99% | 4.99% | 4.99% | 4.99% | 0% |

All of the formulations formed candles. All poured candles developed a single crack near the wick upon cooling, except for candle 123 (Example 123) which showed no signs of cracking. Cracking is a known problem in the art, particularly with vegetable-oil based waxes (see, for example, U.S. Pat. No. 6,503,285) and can generally be mitigated with wax choice, wax blends, cooling rate, additives, and other formulation aspects known in the art.

All of the colored candles showed signs of pigment settling on the bottom of the container candle. Candle 125 exhibited a deeper red color indicative of better pigment incorporation by premixing the pigment with the alkyl ketal ester.

Example 126

This example was conducted to demonstrate the use of a fragrant composition comprising vinallin in a perfume formulation (a candle). The ingredients of the composition are shown in the Table 8 below. The ingredients of the composition were divided into two parts—Part A and Part B, which were then processed as follows: The ingredients of Part B were mixed at room temperature until the vanillin was completely dissolved. In a separate container, the ingredients of Part A were heated at 80° C. until a uniform, molten mixture formed. Part B was then added to part A (while at 80° C.) and mixed until uniform. The vessel containing the Parts A and B were then poured into candle mold. NO wick was added to the candle.

TABLE 8

| Ingredient | Wt % |
|---|---|
| Part A | |
| Paraffin wax | 37.5% |
| Beeswax | 37.5% |
| Part B | |
| Et-LPK | 22.5% |
| vanillin | 2.5% |

A solid, uniform candle formed upon cooling, with no signs of separation.

As can be seen in the examples above, an exemplary fragrant formulation comprises a fragrant composition, an alkyl ketal ester and at least one of (a) a paraffinic, naphthenic, or aromatic mineral oil, (b) a nonionic organic compound having a melting temperature of less than 45° C. and a molecular weight of at least 190 daltons, an amido or ester group, and an alkyl chain containing at least 8 carbon atoms, and a solubility in water of no greater than 1 part in 99 parts of water; (c) a nonionic organosilicone compound having a melting temperature of less than 45° C. with a solubility in water of no greater than 1 part in 99 parts of water; (d) a long chain alcohol; and (e) a wax.

Example 127

Vanillin was dissolved at 10% solids by weight in Et-LGK at room temperature and formed a clear uniform mixture. Vanillin was mixed at 25% solids by weight in Bu-LGK at room temperature. The mixture initially appeared to be insoluble but over the course of five days, the vanillin dissolved, resulting in a clear uniform mixture. Dissolution is much quicker at 80° C.

Vanillin was dissolved at 25% solids by weight in Et-LPK with slight heating (80° C.). The mixtures formed clear uniform solutions hot and stayed as a clear uniform mixture at room temperature initially. Within an hour, signs of precipitation at room temperature appeared. Vanillin was dissolved at 10% solids by weight in Et-LPK at room temperature and formed a clear uniform mixture.

As used herein, the singular forms "a," "an," and "the" are intended to include the plural forms as well, unless the context clearly indicates otherwise. The endpoints of all ranges directed to the same component or property are inclusive of the endpoint and independently combinable, except when the modifier "between" is used. The modifier "about" used in connection with a quantity is inclusive of the stated value and has the meaning dictated by the context (e.g., includes the degree of error associated with measurement of the particular quantity). A "combination" is inclusive of blends, mixtures, alloys, reaction products, and the like.

In general, the formulations or methods can alternatively comprise, consist of, or consist essentially of, any appropriate components or steps disclosed. The invention can additionally, or alternatively, be formulated so as to be devoid, or substantially free, of any components, materials, ingredients, adjuvants, or species, or steps used in the prior art formulations or that are otherwise not necessary to the achievement of the function and/or objectives of the present claims.

Unless otherwise defined, all terms (including technical and scientific terms) used have the same meaning as commonly understood by one of ordinary skill in the art to which this invention belongs. Compounds are described using standard nomenclature. Any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

"Alkyl" means a straight or branched chain saturated aliphatic hydrocarbon having the specified number of carbon atoms. "Alkylene" means a straight or branched divalent aliphatic hydrocarbon group having the specified number of carbon atoms. "Aryl" means a cyclic moiety in which all ring members are carbon and a ring is aromatic. More than one ring can be present, and any additional rings can be independently aromatic, saturated or partially unsaturated, and can be fused, pendant, spirocyclic or a combination thereof. While stereochemistry of the various compounds is not explicitly shown, it is to be understood that this disclosure encompasses all isomers.

All cited patents, patent applications, and other references are incorporated by reference in their entirety.

While the invention has been described with reference to some embodiments, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiments disclosed as the best mode contemplated for carrying out this invention, but that the invention will include all embodiments falling within the scope of the appended claims.

What is claimed is:
1. A fragrant formulation comprising:
   at least one fragrant composition comprising vanillin, and
   an alkyl ketal ester of formula (III) or formula (V)

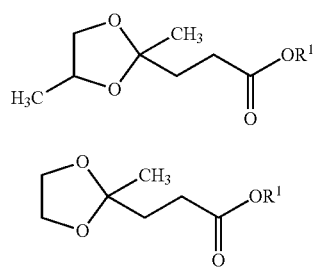

Wherein $R^1$ is methyl, ethyl, n-propyl, or n-butyl.

2. The fragrant formulation of claim 1, wherein the fragrant composition is a flavorant.

3. The fragrant formulation of claim 1, wherein the fragrant composition is a perfume.

4. The fragrant formulation of claim 1, wherein the fragrant composition comprises a perfume and a flavorant.

5. The fragrant formulation of claim 1, wherein the alkyl ketal ester is selected from the group consisting of ethyl-LPK, n-butyl-LPK or combination comprising at least one of the foregoing alkyl ketal esters.

6. The fragrant formulation of claim 1, further comprising at least one of
   (a) a paraffinic, naphthenic, or aromatic mineral oil,
   (b) a nonionic organic compound having a melting temperature of less than 45° C., a molecular weight of at least 190 Daltons,
   an amido or ester group, and
   an alkyl chain containing at least 8 carbon atoms, and
   a solubility in water of no greater than 1 part in 99 parts of water;
   (c) a nonionic organosilicone compound having a melting temperature of less than 45° C., and a solubility in water of no greater than 1 part in 99 parts of water;
   (d) a long chain alcohol; and
   (e) a wax.

7. The fragrant formulation of claim 1, further comprising at least one fully water miscible alkyl ketal ester.

8. The fragrant formulation of claim 1, further comprising at least one partially water-miscible alkyl ketal ester.

9. The fragrant formulation of claim 1, further comprising at least one sparingly water-miscible alkyl ketal ester.

10. The fragrant formulation of claim 1, further comprising water and a partially-or fully water-miscible alkyl ketal ester.

11. The fragrant formulation of claim 1, comprising an alcoholic phase or an alcohol-water mixture.

12. The fragrant formulation of claim 1, in the form of an emulsion comprising an aqueous phase and an oil phase, wherein the aqueous phase comprises the alkyl ketal ester, and the alkyl ketal ester is partially or fully water-miscible.

13. The fragrant formulation of claim 1, in the form of an emulsion comprising an aqueous phase and an oil phase, wherein the oil phase comprises the alkyl ketal ester.

14. The fragrant formulation of claim 1, comprising from about 0.001 to about 40 percent by weight of the fragrant composition, based on the total weight of the formulation.

15. The fragrant formulation of claim 1, further comprising a surfactant.

16. The fragrant formulation of claim 1, further comprising an antioxidant, an antiozonant, an antibacterial agent, a humectant, a colorant, a dye, a pigment, a food additNe, a pheromone, a musk, a carbonate ion source, an alkalizing agent, a pH buffer, a conditioning agent, a chelant, an auxiliary agent, a solvent, a surfactant, a nonsurfactant suspending agent, an emulsifier, a skin conditioning agent, a hair conditioning agent, a hair fixative, a film-former, a skin protectant, a binder, a chelating agent, an antimicrobial agent, an antifungal agent, an antidandruff agent, an abrasive, an adhesive, an absorbent, a deodorant agent, a antiperspirant agent, an opacifying and pearlescing agent, a preservative, a propellant, a spreading aid, a sunscreen agent, a sunless skin tanning accelerator, an ultraviolet light absorber, a pH adjusting agent, a botanical, a hair colorant, an oxidizing agent, a reducing agent, a skin bleaching agent, a pigment, a physiologically active agent, an anti-inflammatory agent, a topical anesthetic, and fragrance solubilizer, a fragrance fixative a polymer, or a combination comprising at least one of the foregoing.

17. The fragrant formulation of claim 1, which is in the form of a candle.

18. A method for preparing the fragrant composition of claim 1 comprising:

blending a flagrant composition comprising vanillin and an alkyl ketal ester of formula (III) or formula (IV)

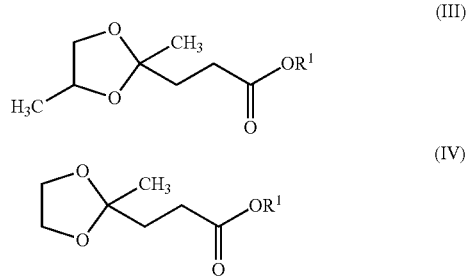

Wherein $R^1$ is methyl, ethyl, n-propyl, or n-butyl.

19. The method of claim 18, further comprising extracting the fragrant composition using the ketal adduct.

20. The method of claim 19, further comprising adding additional alkyl ketal ester to the fragrant composition.

21. The method of claim 19, further comprising removing alkyl ketal ester from the fragrant composition.

22. The method of claim 18, further comprising blending the fragrant composition with a compound, where the compound is an antioxidant, an antiozonant, an antibacterial agent, a humectant, a colorant, a dye, a pigment, a flavoring, a food additive, a pheromone, a musk, a carbonate ion source, an alkalizing agent, a pH buffer, a conditioning agent, a chelant, an auxiliary agent, a solvent, a surfactant, a nonsurfactant suspending agent, an emulsifier, a skin conditioning agent, a hair conditioning agent, a hair fixative, a film-former, a skin protectant, a binder, a chelating agent, an antimicrobial agent, an antifungal agent, an antidandruff agent, an abrasive, an adhesive, an absorbent, a dye, a deodorant agent, a antiperspirant agent, an opacifying and pearlescing agent, a preservative, a propellant, a spreading aid, a sunscreen agent, a sunless skin tanning accelerator, an ultraviolet fight absorber, a pH adjusting agent, a botanical, a hair colorant, an oxidizing agent, a reducing agent, a skin bleaching agent, a pigment, a physiologically active agent, an anti-inflammatory agent, a topical anesthetic, a perfume and perfume solubilizer, a polymer, or a combination comprising at least one of the foregoing.

23. An article comprising the fragrant composition of claim 1.

24. The article of claim 23, which is selected from the group consisting of body lotions, shampoos, massage oils, perfume sticks and lanterns, air fresheners, candles, paints, varnishes, furniture care, insect repellents, in polymers, cleaners, detergents, cosmetics, toiletries, cosmeceuticals and beauty aids, and personal hygiene and cleansing products applied to the skin, hair, scalp, and nails of humans and animals.

25. The article of claim 23, which is in the form of a household care product.

26. The article of claim 23, which is in the form of a health care product.

27. The formulation of claim 1, wherein the formulation comprises 15 wt. % to 70 wt. % of the alkyl ketal ester of formula (III) or formula (IV) and 0.1 to 5 wt. % of the fragrant composition, all based on the total weight of the fragrant formulation.

28. The fragrant formulation of claim 1, wherein the formulation comprises about 2.5 wt % to about 25 wt % of vanillin.

29. The fragrant formulation of claim 1, wherein the formulation comprises about 10 wt % to about 25 wt % of vanillin.

30. The method of claim 18, wherein the composition comprises about 2.5 wt % to about 25 wt % of vanillin.

31. The method of claim 18, wherein the composition comprises about 10 wt % to about 25 wt % of vanillin.

* * * * *